United States Patent
Leak et al.

(10) Patent No.: US 9,402,961 B2
(45) Date of Patent: Aug. 2, 2016

(54) DRUG DELIVERY DEVICE HAVING A SPRING ELEMENT

(75) Inventors: David Martin Leak, Lake Hopatcong, NJ (US); Malcolm Stanley Boyd, Warwickshire (GB); Daniel Thomas De Sausmarez Lintell, Warwickshire (GB); Simon Lewis Bilton, Warwickshire (GB); Daniel David Higgins, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 375 days.

(21) Appl. No.: 13/885,326

(22) PCT Filed: Nov. 28, 2011

(86) PCT No.: PCT/EP2011/071117
§ 371 (c)(1),
(2), (4) Date: May 14, 2013

(87) PCT Pub. No.: WO2012/072541
PCT Pub. Date: Jun. 7, 2012

(65) Prior Publication Data
US 2013/0245565 A1 Sep. 19, 2013

Related U.S. Application Data

(60) Provisional application No. 61/433,683, filed on Jan. 18, 2011.

(30) Foreign Application Priority Data

Nov. 29, 2010 (EP) .................................... 10192835

(51) Int. Cl.
*A61M 5/315* (2006.01)
*A61M 5/19* (2006.01)
(Continued)

(52) U.S. Cl.
CPC ............. *A61M 5/31548* (2013.01); *A61M 5/19* (2013.01); *A61M 5/3156* (2013.01);
(Continued)

(58) Field of Classification Search
CPC ............. A61M 5/19; A61M 5/31525; A61M 5/31548; A61M 5/31551; A61M 5/3156; A61M 5/31561; A61M 5/31585; A61M 5/31593
See application file for complete search history.

(56) References Cited

U.S. PATENT DOCUMENTS

| | | | |
|---|---|---|---|
| 5,378,233 | A | 1/1995 | Haber et al. |
| 8,651,338 | B2 * | 2/2014 | Leak et al. |

(Continued)

FOREIGN PATENT DOCUMENTS

| | | |
|---|---|---|
| JP | H07-509636 | 10/1995 |
| JP | 2006-526467 | 11/2006 |

(Continued)

OTHER PUBLICATIONS

International Preliminary Report on Patentability for Int. App. No. PCT/EP2011/071117, mailed Jun. 13, 2013.

(Continued)

*Primary Examiner* — Aarti B Berdichevsky
(74) *Attorney, Agent, or Firm* — McDonnell Boehnen Hulbert & Berghoff LLP

(57) ABSTRACT

A drug delivery device having a spring element that provides dispense assistance. The drug delivery device includes a variable dose setting mechanism, a fixed dose setting mechanism, and a mechanical coupling having a spring element. The variable dose setting mechanism is operably coupled to a first reservoir holding a first medicament, and the variable dose setting mechanism comprises a dose setter. The fixed dose setting mechanism is operably coupled to a second reservoir holding a second medicament. The mechanical coupling operably couples the variable dose setting mechanism and the fixed dose setting mechanism. Further, the variable dose setting mechanism is configured to set a variable dose of the first medicament upon activation of the dose setter, and the fixed dose setting mechanism is configured to set a fixed dose of the second medicament during variable dose setting. Still further, the spring element is configured to store energy during dose setting and to transfer stored energy to the fixed dose setting mechanism to assist with dispense of the fixed dose.

14 Claims, 12 Drawing Sheets

(51) Int. Cl.
*A61M 5/20* (2006.01)
*A61M 5/24* (2006.01)

(52) U.S. Cl.
CPC ...... *A61M 5/31525* (2013.01); *A61M 5/31551* (2013.01); *A61M 5/31561* (2013.01); *A61M 5/31585* (2013.01); *A61M 5/20* (2013.01); *A61M 5/24* (2013.01); *A61M 5/3157* (2013.01); *A61M 5/31593* (2013.01); *A61M 2005/202* (2013.01)

(56) References Cited

U.S. PATENT DOCUMENTS

| | | | |
|---|---|---|---|
| 9,089,645 B2 * | 7/2015 | Leak et al. | |
| 2007/0060894 A1 | 3/2007 | Dai et al. | |
| 2012/0125951 A1 * | 5/2012 | Leak et al. | |
| 2013/0231613 A1 * | 9/2013 | Leak et al. | |
| 2013/0237924 A1 * | 9/2013 | Leak et al. | |
| 2013/0245566 A1 * | 9/2013 | De Sausmarez Lintell et al. | |
| 2013/0267908 A1 * | 10/2013 | Leak et al. | |

FOREIGN PATENT DOCUMENTS

| | | |
|---|---|---|
| WO | 94/03392 | 2/1994 |
| WO | 94/22507 | 10/1994 |
| WO | 2004/108193 | 12/2004 |
| WO | 2010/077279 | 7/2010 |
| WO | 2010/077280 | 7/2010 |

OTHER PUBLICATIONS

International Search Report and Written Opinion for Int. App. No. PCT/EP2011/071117, completed Jan. 4, 2012.

Chinese Office Action for CN App. No. 201180066267.5, dated Sep. 11, 2014.

Japanese Office Action for JP App. No. 2013-540392, mailed Nov. 4, 2015.

* cited by examiner

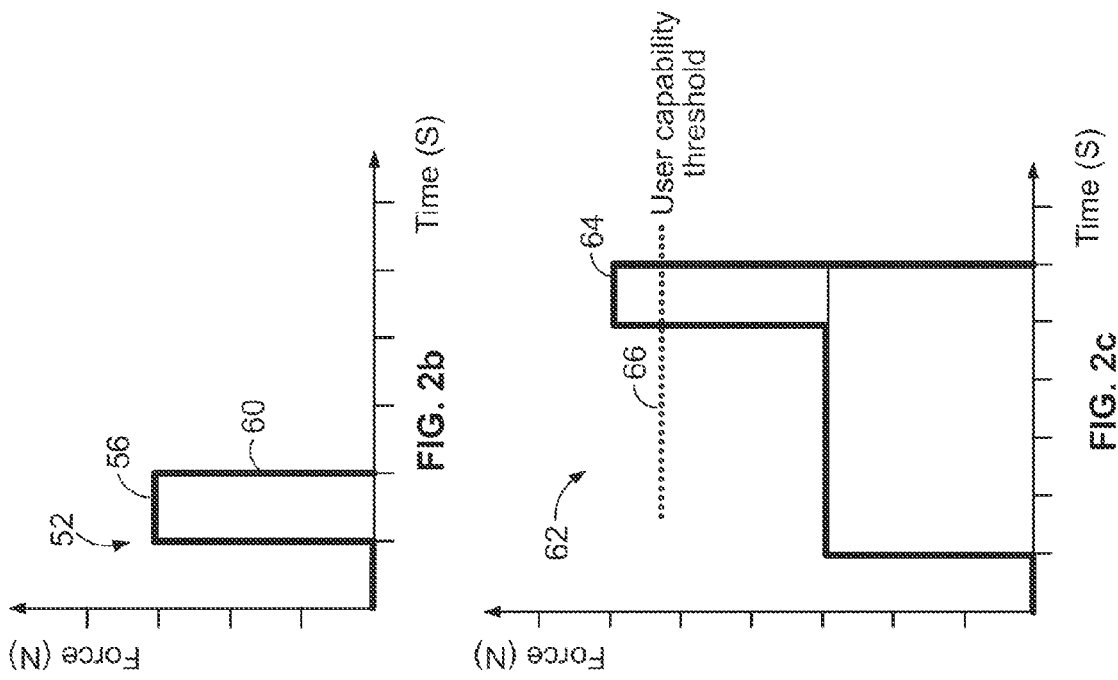
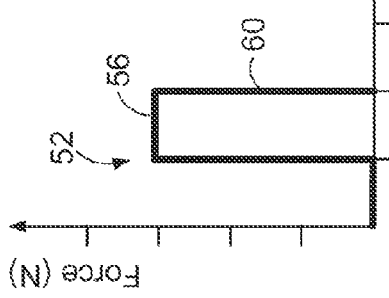
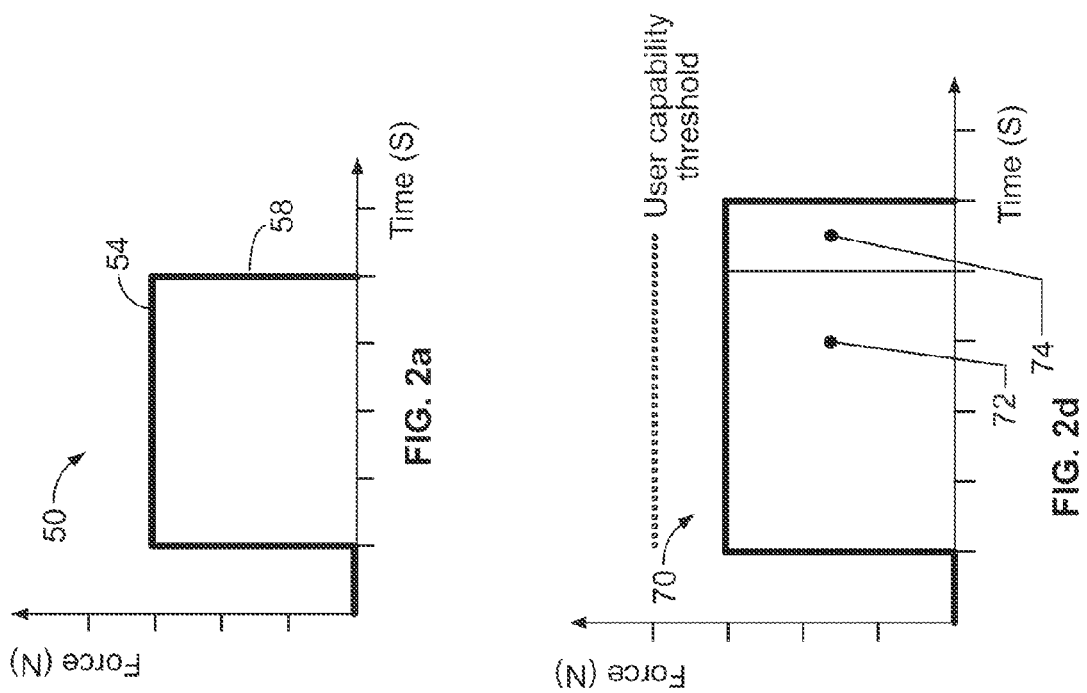

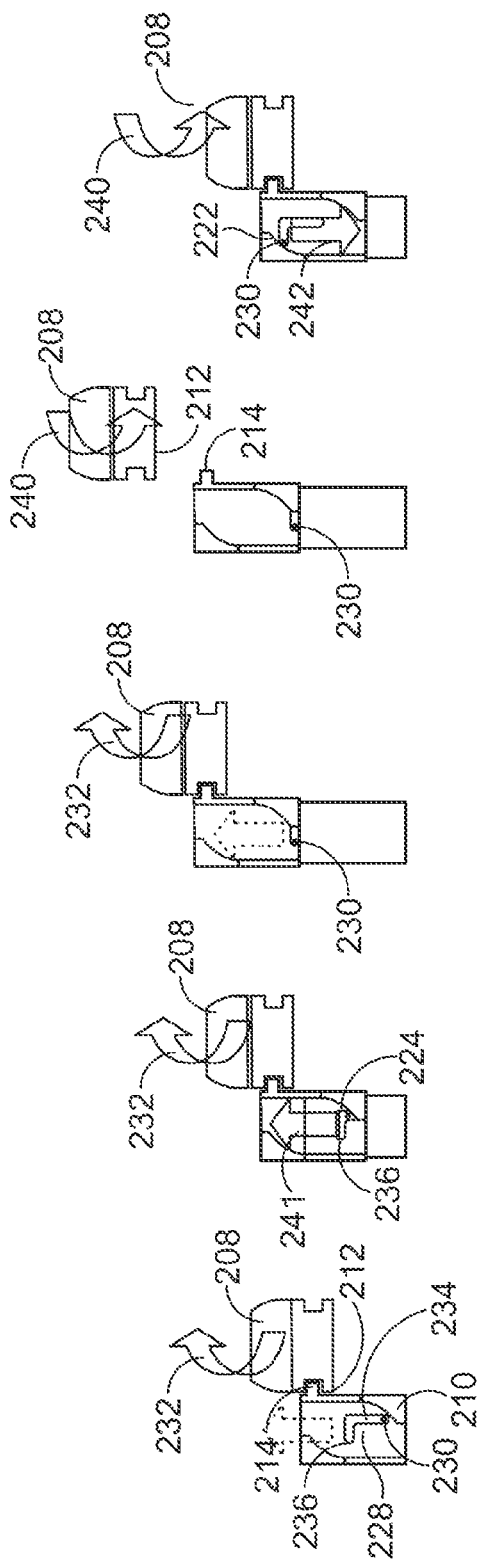

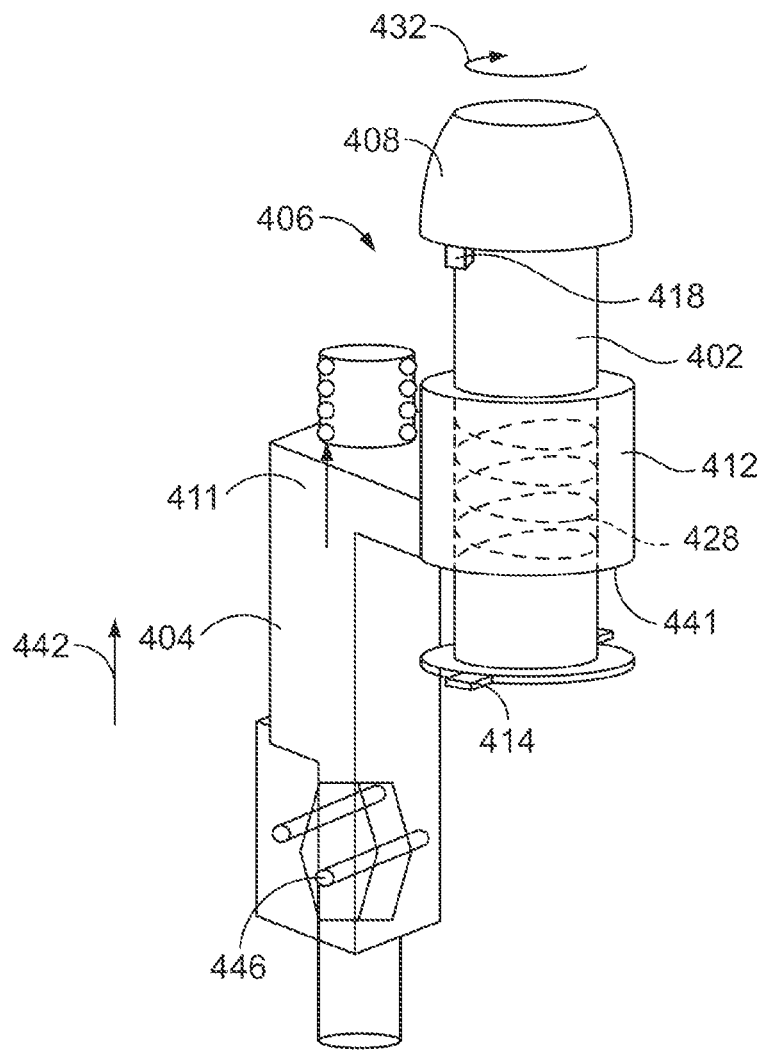
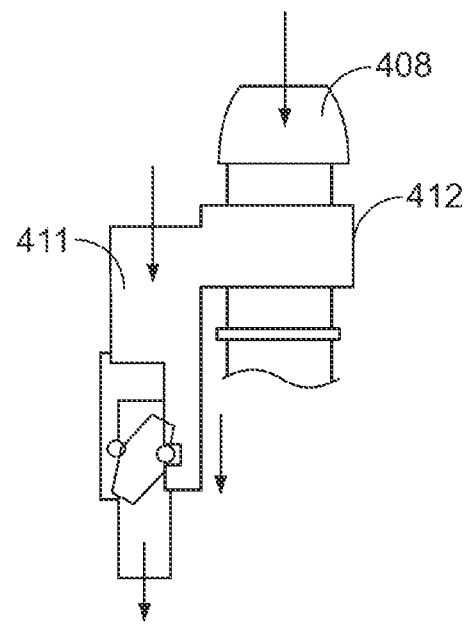
FIG. 8a
FIG. 8b

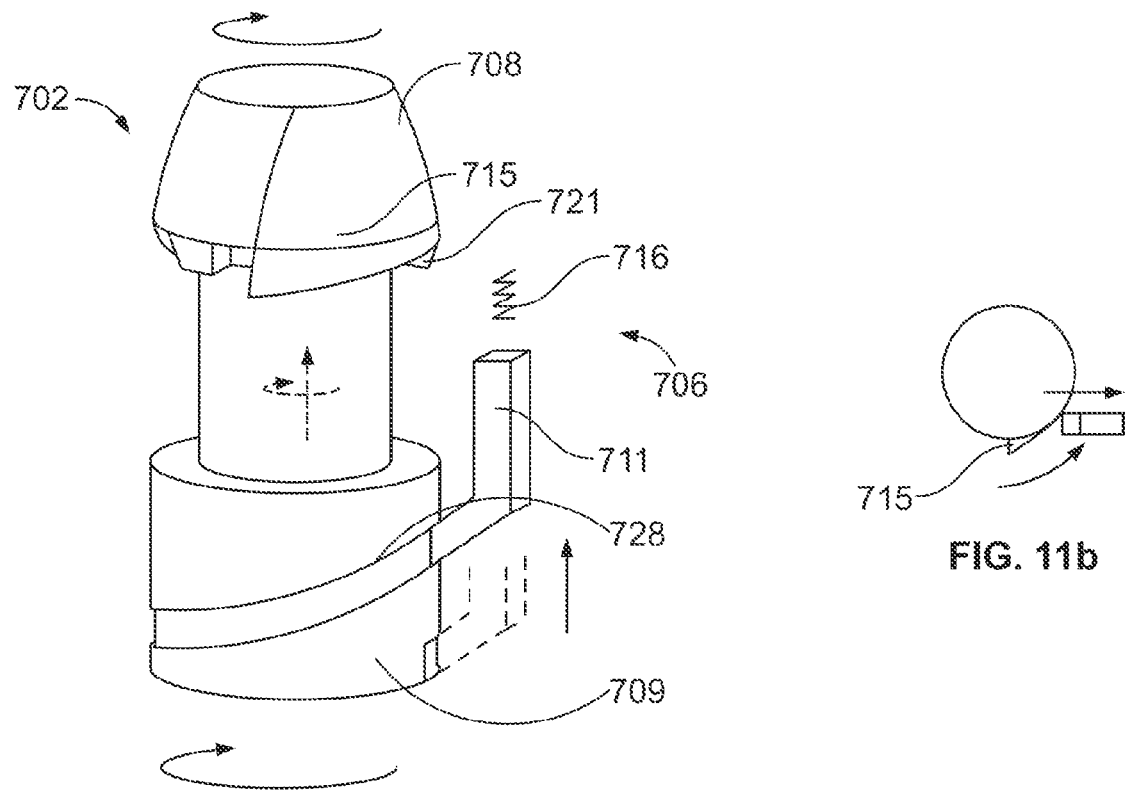
FIG. 11a
FIG. 11b
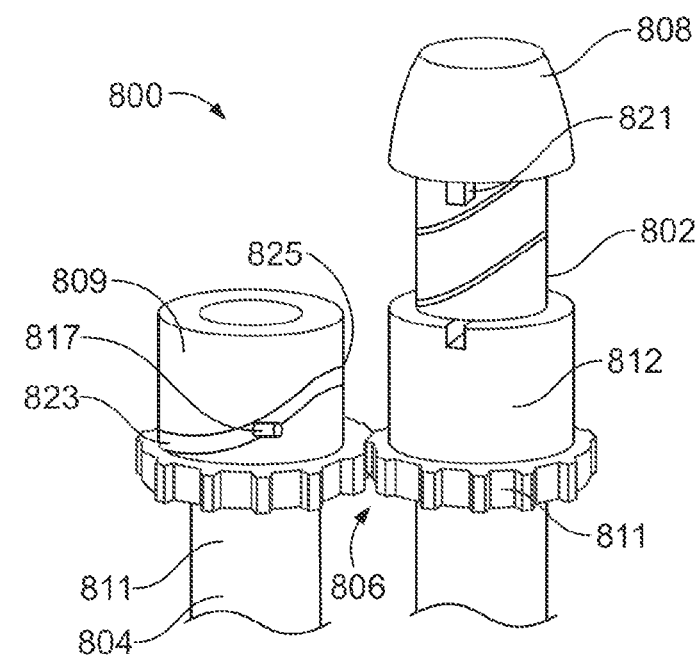
FIG. 12a

DRUG DELIVERY DEVICE HAVING A SPRING ELEMENT

CROSS REFERENCE TO RELATED APPLICATIONS

The present application is a U.S. National Phase Application pursuant to 35 U.S.C. §371 of International Application No. PCT/EP2011/071117 filed Nov. 28, 2011, which claims priority to European Patent Application No. 10192835.6 filed Nov. 29, 2010 and U.S. Provisional Patent Application No. 61/433,683, filed Jan. 18, 2011. The entire disclosure contents of these applications are herewith incorporated by reference into the present application.

FIELD OF THE DISCLOSURE

This present patent application relates to medical devices and methods of delivering at least two drug agents from separate reservoirs using devices having only a single dose setter and a single dispense interface. A single delivery procedure initiated by the user causes a non-user settable or fixed dose of a second drug agent and a user settable or variable set dose of a first drug agent to be delivered to the patient. The drug delivery device may include a spring element that is configured to assist with the delivery of the second drug agent. The drug agents are contained in two or more multiple dose reservoirs, containers or packages, each containing independent (single drug compound) or pre-mixed (co-formulated multiple drug compounds) drug agents. The disclosed method and system is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. The disclosed method and system is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties.

An additional issue that may arise is a potentially high dispense force required to inject a drug compound or two drug compounds. Dispense force is generally proportional to the amount of fluid being dispensed over a given time and the resistance (e.g., hydraulic resistance) through the device. A higher dose may therefore require a higher dispense force. Further, because a dual injection device injects two drug compounds rather than a single drug compound, the dispense force required by a dual injection device may be higher than a dispense force required by a typical single compound drug delivery device. For instance, dual injection devices may also have to overcome two sets of delivery mechanism frictions and/or two bungs moving in two cartridges.

Fully automatic devices may reduce or eliminate the force required to inject a drug compound or two drug compounds. However, fully automatic devices that have the capability to fully inject all drug compounds may experience 'push-back' from some users due to the lack of user control during dispensing. For example, certain users/patients express the desire or need to have at least a given level of control over the dispensing process (e.g., be required to use some manual input to dispense the medicaments). Fully automatic devices have the further disadvantage of having to exert a high magnitude of force to account for the force variability and the requirement to ensure sufficient margin between the force delivered and the force required in all dose scenarios.

SUMMARY

Accordingly, there exists a strong need to provide devices and methods for the delivery of two or more medicaments in a single injection or delivery step that is simple for the user to perform. Further, there exists a need to provide devices and methods that reduce the dispense force for delivery of two or more medicaments in a single injection or delivery step, while at the same time allowing the user a degree of control over the dispense.

The disclosed method and system overcomes the above-mentioned problems by providing separate storage containers for two or more active drug agents that are then only combined and/or delivered to the patient during a single delivery procedure. The disclosed method and system also provides biasing element such as a spring that is configured to reduce the dispense force required by the device. Setting a dose of one medicament automatically fixes or determines the dose of the second medicament (i.e. non-user settable). The disclosed method and system also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. Alternatively, the second fluid quantity can be changed by varying the properties of the fixed dose mechanism. The disclosed system and method may achieve a wide variety of target therapeutic profiles. For example, the disclosed system and method may achieve a therapeutic profile that delivers a fixed dose of a secondary medicament once a minimum setting threshold dose of a primary medicament has been set.

The disclosed system and method also may add an element of auto-assistance that reduces the dispense force for the injection of two (or more) drug compounds while allowing the user a degree of control over the dispense process.

These and other advantages will become evident from the following more detailed description of the invention.

The disclosed system and method allows complex combination of multiple drug compounds within a single device. The disclosed system and method also provides for auto-assistance that reduces the dispense force for the injection of multiple drug compounds within the single device. In particular, the disclosed system and method allows the user to set and dispense a multi-drug compound device through one single dose setting mechanism and a single dispense interface, and the system includes a spring element that provides for auto-assistance that reduces the dispense force. This single dose setter controls the dose setting of the device such that a predefined combination of the individual drug compounds is delivered when a single dose of one of the medicaments is set and dispensed through the single dispense interface. Although principally described in this application as an injection device, the basic principle could be applicable to other forms of drug delivery, such as, but not limited to, inhalation, nasal, ophthalmic, oral, topical, and like devices.

By defining the therapeutic relationship between the individual drug compounds, Applicants' delivery device would help ensure that a patient/user receives the optimum therapeutic combination dose from a multi-drug compound device without the inherent risks associated with multiple inputs, where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

This disclosed system is of particular benefit to users with dexterity or computational difficulties as the single input and associated predefined therapeutic profile removes the need for them to calculate their prescribed dose every time they use the device and the single input allows considerably easier setting and dispensing of the combined compounds.

In an embodiment of the proposed system, a master drug compound, such as insulin, is contained within a primary reservoir and a secondary medicament is contained within a secondary reservoir. When a dose of the primary compound is set and dispensed, the secondary compound is set and delivered. Although Applicants' present patent application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed system and method.

For the purposes of Applicants' system and method the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of Applicants' disclosure relates to a drug delivery system to deliver two or more medicaments through a single dose setter and a single dispense interface, where the device has a housing containing a single user-operable dose setter operably connected to a primary reservoir of a first medicament containing multiple doses of at least one drug agent. A dose button is operably connected to the primary reservoir of medicament and a single dispense interface is configured for fluid communication with the primary reservoir. A secondary reservoir of a second medicament containing multiple doses of at least one drug agent is configured for fluid communication to the single dispense interface. A single activation of the dose setter by a user sets a dose from the primary reservoir and automatically sets a non-user settable dose of the second medicament. A single activation of the dose button causes the set dose of the first medicament from the primary reservoir and the set non-user settable dose of the second medicament to be expelled through the single dispense interface. A secondary fixed dose setting mechanism may be operably connected to a spring element that is configured to at least assist with dispense of the secondary medicament.

This dose button can be any type of mechanism that triggers the delivery procedure. Applicants' system has a single dispense interface configured for fluid communication with the primary reservoir and with a secondary reservoir of medicament containing at least one drug agent. The drug dispense interface can be any type of outlet that allows the two or more medicaments to exit the system and be delivered to the patient. Types of interfaces include hollow needles, catheters, atomizers, pneumatic injectors, or needle-less injectors, mouthpieces, nasal-applicators and the like interfaces.

According to one aspect of the invention the dose setter and the dose button are arranged and designed as one element for proving the two functionalities. This provides for simple and safe use of a device. The use of a device for the delivery of two or more medicaments is thus very similar to that of a single medicament device, such as a pen-type injector. Thus user compliance and comfort is increased by means of this feature.

The secondary reservoir contains multiple doses of medicament. As mentioned above, the system is designed such that a single activation of the dose button causes the user set dose of medicament from the primary reservoir and a non-user set dose of medicament from the second reservoir to be expelled through the single dispense interface. By user settable dose it is meant dose that the user (patient or health care provider) can physically manipulate the device to set a desired dose. Additionally, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. In other words, when the user (or another input as described above) sets the dose of the primary medicament in the primary reservoir, the dose of the second medicament is automatically set.

According to one aspect of the invention a variable dose setting mechanism enables a user (e.g. patient, health care provider, etc.) to select and set a dose according to the patient's needs each time the medicament is to be administered. The dose is user settable or variable. The dose is variable in the sense that it may be different at each time of administration. However, dialing the same dose is also feasible.

According to another aspect of the invention a fixed dose setting mechanism enables a user (e.g. patient, health care provider, etc.) to prepare the device for administration of a pre-set or fixed amount of medicament. The dose is non-user settable or non-adjustable or fixed. The dose is fixed in the sense that it may not be changed by the user. However, the device may require the dose to be set in order to prepare dispensing the fixed or non-user set dose.

In an example of Applicants' proposed system, a drug delivery device includes a variable dose setting mechanism, a fixed dose setting mechanism, and a mechanical coupling having a spring element. The variable dose setting mechanism is operably coupled to a first reservoir holding a first medicament, and the variable dose setting mechanism comprises a dose setter. The fixed dose setting mechanism is operably coupled to a second reservoir holding a second medicament. The mechanical coupling operably couples the variable dose setting mechanism and the fixed dose setting mechanism. Further, the variable dose setting mechanism is configured to set a variable dose of the first medicament upon activation of the dose setter, and the fixed dose setting mechanism is configured to set a fixed dose of the second medicament during dose setting. Setting the fixed dose may be automatic. Still further, the spring element is configured to store energy during dose setting and to transfer stored energy to the fixed dose setting/dispensing mechanism to at least assist with dispense of the fixed dose.

According to the invention, the mechanical coupling operably couples the variable dose setting mechanism and the fixed dose setting mechanism during dose setting. The mechanical coupling operably couples the variable dose setting mechanism and the fixed dose setting mechanism during dispense.

Applicants' present disclosure also covers a method of dispensing a fixed dose of one medicament and a variable dose of a second medicament from separate reservoirs that involves the steps of first setting a dose of a first medicament contained in a primary reservoir of a drug delivery device having a single dose setter. This setting of the first dose automatically sets the dose from a secondary reservoir without a separate input by the user. Next a dose button is activated that moves both the set dose of the first medicament from the primary reservoir and the automatically set non-user settable dose from the secondary reservoir through a single dispense interface. The method further comprises compressing a spring element during setting of the user settable dose.

The combination of compounds as discrete units or as a mixed unit can be delivered to the body via an integral needle. This would provide a combination drug injection system that, from a user's perspective, would be achieved in a manner that very closely matches the currently available injection devices that use standard needles. One possible delivery procedure would involve the following steps:

Attach a single dispense interface, such as a needle hub, to the distal end of the injection device such that the proximal end of the single dispense interface is in fluidic communication with both the primary compound and secondary compound.

Dial up (i.e., set) the injection device such that it is ready to dispense the desired dose of the primary compound. As the single dose setter sets the dose of the primary compound, a predefined non-user settable dose of the secondary compound is automatically set at the same time. In addition, a spring element is compressed as the fixed dose is set.

Insert or apply the distal end of the single dispense interface to the patient at or into the desired administration site. Dose the primary compound by activating a single dose button, which also causes the secondary compound to automatically dispense, with auto-assistance provided by a compressed spring element to reduce the dispense force.

The drug delivery system of Applicants' disclosure may be designed in such a way as to limit its use to exclusive primary and secondary reservoirs through employment of dedicated or coded features.

A particular benefit of Applicants' proposed system and method is that the use of two multi-dose reservoirs makes it is possible to tailor dose regimes when required, especially where a titration period is necessary for a particular drug. In an example, a set of drug delivery devices may be provided that have second dose setting mechanisms and/or reservoirs that have different properties, and thus result in different fixed doses of a second medicament. The drug delivery devices could be supplied in a number of titration levels with obvious differentiation features such as, but not limited to, aesthetic design of features or graphics, numbering etc, so that a user could be instructed to use the supplied_drug delivery devices in a specific order to facilitate titration. Alternatively, the prescribing physician may provide the patient with a number of "level one" titration drug delivery devices and then when these were finished, the physician could then prescribe the next level.

Another particular benefit of Applicants' proposed system is that the system provides an element of auto-assistance that reduces the dispense force for the injection of two (or more) drug compounds while allowing the user a degree of control over the dispense process.

A further feature of an example of Applicants' proposed system and method is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 2a illustrates an example force profile for dispensing a first medicament;

FIG. 2b illustrates an example force profile for dispensing a second medicament;

FIG. 2c illustrates an example force profile for dispensing both the first medicament of FIG. 2a and the second medicament of FIG. 2b in combination;

FIG. 2d illustrates another example force profile for dispensing both the first medicament of FIG. 2a and the second medicament of FIG. 2b in combination;

FIGS. 6a-e depict the drug delivery device of FIG. 5 during various phases of the operation of the drug delivery device;

FIGS. 8a-b illustrates a partial view of yet another example drug delivery device in accordance with an embodiment of Applicants' proposed concept;

FIG. 9b illustrates a perspective view of the dose setter of the drug delivery device depicted in FIG. 9a;

FIG. 10b illustrates a cross-section of the lifting collar of the drug delivery device depicted in FIG. 10a;

FIG. 11a depicts a partial view of an example variable dose mechanism for an example drug delivery device in accordance with an embodiment of Applicants' proposed concept;

FIG. 11b illustrates a cross-section view of the variable dose mechanism of FIG. 11a;

FIG. 12a illustrates a partial view of yet another example drug delivery device in accordance with an embodiment of Applicants' proposed concept;

FIG. 12b illustrates a cross-section of the cam of the drug delivery device depicted in FIG. 12a;

FIG. 13b illustrates an exploded view of the fixed dose setting mechanism of the drug delivery device illustrated in FIG. 13a; and FIG. 13c illustrates a close-up view of the spring arm and escapement depicted in FIG. 13b.

DETAILED DESCRIPTION

Figure 1:
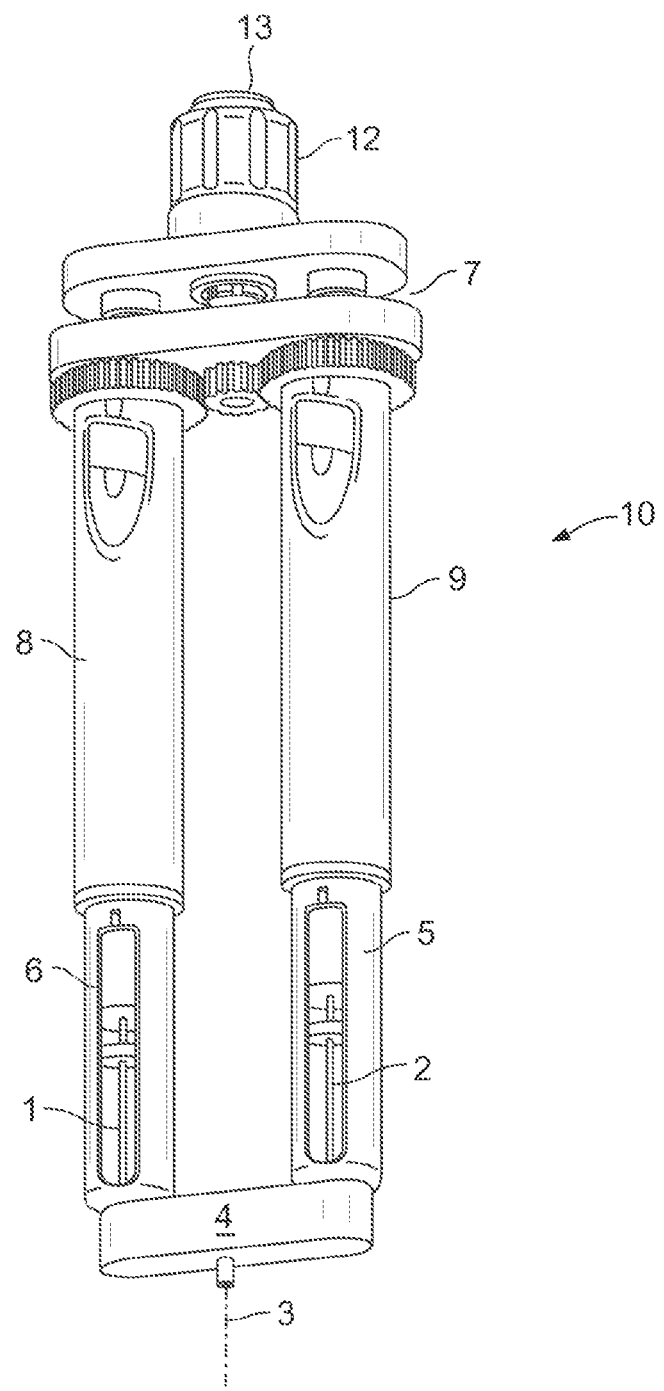
FIG. 1 illustrates a drug delivery system in accordance with an example of Applicants' disclosure, the drug delivery system having two multi-dose reservoirs positioned side-by-side containing a primary medicament and a secondary medicament, respectively.

The drug delivery system of the present disclosure administers a non-user settable or fixed or predetermined dose of a second medicament (secondary drug compound) and a variable dose of a first medicament (primary drug compound) through a single output or drug dispense interface. Setting the dose of the primary medicament by the user automatically determines the fixed dose of the second medicament. In an example the drug dispense interface is a needle cannula (hollow needle). FIG. 1 generally illustrates a multi-dose injection device that is capable of setting and delivering both a dose of a first medicament and a dose of a second medicament via a single dose setter and a single dispense interface. Such an injection device may be modified to comprise a spring element that is capable of assisting with delivery of the medicament. FIGS. 5-13 illustrate possible examples of drug delivery devices according to Applicant's proposed concept that include a spring element capable of assisting with delivery of the medicament.

In particular, FIG. 1 illustrates one possible example of a drug delivery system, where a multi-use injection device 10 has two reservoirs that are positioned side-by-side with one containing a first medicament 1 and the other a second medicament 2. These reservoirs may contain multiple doses of each medicament. Each reservoir may be self-contained and provided as sealed and sterile cartridges. These cartridges can be of different volumes and replaceable when empty or they can be fixed (non-removable) in the system. They can also have pierceable seals or septa to accept needle cannula.

The cartridges may be housed in cartridge holders 5 and 6 that have attachment means compatible with a removable, disposable hub or housing 4 that contains the single dispense interface. In this example the single dispense interface is shown as output needle 3. The hub can be of any design, provided that it allows for fluid communication between the primary and secondary medicaments and the single dispense interface or needle 3. An example design of hub 4 would include what is referred to in the art as a "2-to-1 needle" configuration. Although not shown, hub 4 could be supplied by a manufacturer contained in a protective and sterile capsule or container where the user would peel or rip open a seal or the container itself to gain access to the sterile single dispense interface. In some instances it might be desirable to provide two or more seals for each end of the hub. The seal may allow display of information required by regulatory labeling requirements. When a needle is used to deliver the medicaments it is preferred that the hub is designed to be economical and safe for allowing the user to attach a new hub for each injection. Attachment of hub 4 to the multi-use device 10 creates a fluid connection between output needle 3 and medicaments 1 and 2.

The example in FIG. 1 uses a rotational coupling 7 to mechanically link two dose delivery assemblies 8 and 9 in such a way that rotation of single dose setter 12 allows the user to select a dose of the primary medicament 1 and automatically set a fixed or predetermined non-user settable dose of secondary medicament 2. In the example illustrated, the rotational coupling 7 has been embodied as a gear train in which counter-clockwise rotation of the single dose setter causes clockwise rotation of dose dial components (not shown) within the dose delivery assemblies 8 and 9. The fact that both dial components rotate in the same direction (i.e. clockwise) may allow both dose delivery assemblies to be of similar construction in terms of the direction of the helically threaded components and is also likely to be intuitive for a user to understand. Rotational coupling 7 may be constructed such that it moves vertically at the same rate as both of the dial components. This allows it to set and dispense both drug compounds throughout the full operational range of the device.

As well understood by those skilled in the art, it is convenient to use lead screws or spindles to push on a piston or bung contained within a cartridge of medicament. As such, the dose delivery assemblies may include spindles. By varying the spindle pitches it is possible to vary the dose sizes (and dose ratio) in relation to each other. Specifically, this allows variation of the therapeutic profile to suit a specific therapy or patient requirements by providing devices with different dose ratios. The device shown in FIG. 1 could be operated as follows:

Counter-clockwise rotation of the dose setter 12 causes counter-clockwise rotation of the drive gear and clockwise rotation of both driven gears in rotational coupling 7. Clockwise rotation of both driven gears forces both dial components in dose delivery assemblies 8 and 9 to rotate in the same direction and follow a helical path out of the body of the device. This operation allows the user to set a target dose of medicament 1, but not medicament 2, which is automatically set by whatever dose is selected for medicament 1.

Initiation of the dosing phase begins with the actuation of dispense or dose button 13 by the user. This causes the dial components to rotate independently of the dose setter.

During the dosing phase, the direction of rotation of the single dose setter as well the internal components of both device mechanisms is reversed. The rotational coupling 7 moves back towards the body of the device as both dial components wind back into the mechanisms following their respective helical paths. This reversal of rotation of both mechanisms coupled with the internal overhauling of the spindles by internal drive sleeves (not shown) causes both medicaments to be dispensed in a simultaneous fashion following the fixed ratio profile defined when the user set the target dose of medicament 1.

Varying the spindle pitches of the individual device mechanisms in relation to each other may alter the relationship of the fixed ratio of medicaments. Variation of the spindle pitch changes the advance of the spindle during dispense for a given amount of rotation during setting. Differing amounts of advance between the two mechanisms has the effect of creating different dispense ratios between the mechanisms. Variation of the spindle pitches may have the effect of extending the operational window of delivery device 10 in terms of the range of fixed ratios that can be achieved. This may also assist in keeping the spindle pitch in a range that allows resetting should the device be required to be reusable. This means that multiple pen injectors each having a different therapeutic profile can be manufactured. Specifically, this allows variation of the therapeutic profile to suit a specific titration regime and ultimately individual patient requirements.

The attachment means between hub 4 and cartridge holders 5 and 6 can be any known to those skilled in the art, including threads, snap locks, snap fits, luer locks, bayonet, snap rings, keyed slots, and combinations of such connections. The connection or attachment between the hub and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary reservoir to a non-matching injection device.

The shape of the dispense device 10, including hub 4, may be generally oval and/or cylindrical or any other geometric shape suitable for hand manipulation by a user. Additionally, hub 4 could incorporate a safety shield device that would prevent accidental needle sticks and reduce the anxiety experienced by users who suffer from needle phobia. The exact design of the safety shield is not critical to Applicants' drug delivery device, however, an example design is one that is operably connected to the first and/or second reservoirs. In such a design the activation of the safety shield could unlock the drug delivery system or instigate fluid communication between the reservoirs and in some cases cause the second medicament to be dispensed prior to activating the dose button to dispense the primary medicament from the first reservoir. Another example design would physically prevent insertion of the used drug dispense interface into the patient (e.g. a single use needle-guard type arrangement).

As mentioned an example design of Applicants' drug delivery device would include cartridges to contain the medicaments. Cartridges are typically cylindrical in shape and are usually manufactured in glass, sealed at one end with a rubber bung (piston) and at the other end by a rubber septum using a metal ferrule. The dose delivery assemblies are typically powered by a manual action of the user, however, the injection mechanism may also be powered by other means such as a spring, compressed gas or electrical energy.

In accordance with Applicants' proposed concept, a drug delivery device such as the device 10 illustrated in FIG. 1 may include a spring element that assists with the dispense of at least one of the medicaments. Various example mechanical links having such a spring element are described below with reference to FIGS. 5-13. The example of FIG. 1 depicts a mechanical link between two dose setting mechanisms that are each configured to rotationally set a dose. However, it should be understood that the mechanical link may link other types of dose setting mechanisms. For instance, a rotationally-set dose setting mechanism may be linked to an axially-set dose setting mechanism.

As mentioned above, a drug delivery device configured to deliver two medicaments may require a high dispense force to inject the two medicaments. FIG. 2a-b depict example force profiles for two medicaments when injected separately, and FIG. 2c depicts an example force profile for the two medicaments when injected together. In particular, FIG. 2a depicts a force profile 50 for injecting a first, primary medicament, and FIG. 2b depicts a force profile 52 for injecting a second, secondary medicament. As can be seen from FIGS. 2a-b, for the separate injection of the first and second medicaments, the force increases sharply to a plateau region 54, 56 throughout which it is typically constant, followed by a steep drop-off 58, 60 when the dispensing is finished.

Rather than being injected separately from two separate devices, however, these two medicaments may be injected using a single device, such as device 10. The force profile for the combined device may generally be a summation of the two force profiles 50, 52. FIG. 2c depicts an example dose profile 62, where the second medicament is injected toward the end of the injection of the first medicament. It should be understood, however, that the second medicament may be dispensed at other times (i.e., anywhere throughout the dispense cycle of the first medicament), thus resulting in different possible force profiles. Further, in this example, the dispense duration of the first medicament is longer than the dispense duration of the second medicament. It should be understood, however, that dispense durations different than the depicted dispense durations are possible.

As most pen-type drug delivery devices require manual operation to generate sufficient force to dispense the medicament, it is advantageous for the resultant amount of force required to be within a user's capability. Generally, it is beneficial for the resultant amount of force required to be within the user capability of the target population, including those with limited capability (such as, for example, geriatrics or pediatrics) whose capability to exert force may be below that of an average user.

As shown in FIG. 2c, a maximum force 64 required exceeds a user capability threshold 66. Example experimental values of force required to dispense medicaments from two drug reservoirs may be in excess of 18 newtons (N) (for an example assumed flow rate). However, in an example, the target user population's force capability may be around 14 N (e.g., based on a given percentile value from a sample of diabetic patients). Thus, the dispense force required for dispensing two medicaments may be greater than the force capability of a given set of users. Applicants proposed drug delivery system beneficially is capable of performing an auto-assist function to the dispense process of the drug delivery device, thereby decreasing the force required to dispense medicament.

An example idealized force profile 70 for dispensing two medicaments is shown in FIG. 2d. Profile 70 includes a first section 72, which includes the force for injecting a first medicament, and a second section 74, which includes the force profile for injecting the second medicament. Such an idealized force profile may be difficult to achieve in practice due to (i) variations in dispense force required between the medicament reservoirs and (ii) timing issues. Another issue associated with dispensing multiple medicaments is the variability of dispense force between two medicaments arising in ways such as (but not limited to) reservoir frictional differences, fluid viscosity differences, cartridge parameter differences (diameter), volumetric flow differences, etc. A possible consequence of these differences may be that the dispense force will likely be slightly different for both reservoirs. Further, this may result in a step change in dispense force during the transition from dispensing the first medicament to the transition to dispensing the second medicament. This may, depending on the user's interpretation, create an issue of giving false feedback to the user that suggests that either the dose/dispense stroke is finished or that there is a defect or problem with the device. The problem of incorrect feedback may be more prevalent with force "step-up" changes.

Applicants' disclosed system and method provides for a drug delivery device that includes an auto-assistance feature; however, the disclosed system is not a fully automatic device. In accordance with Applicants' proposed concept, the force profile of a drug delivery device may be altered by mechanical means of storing and releasing energy, such as through the use of a biasing element. Potential results of altering the dose profile by mechanical means of storing and releasing energy are discussed below with reference to FIGS. 3a-b and 4a-e.

Figure 3A:
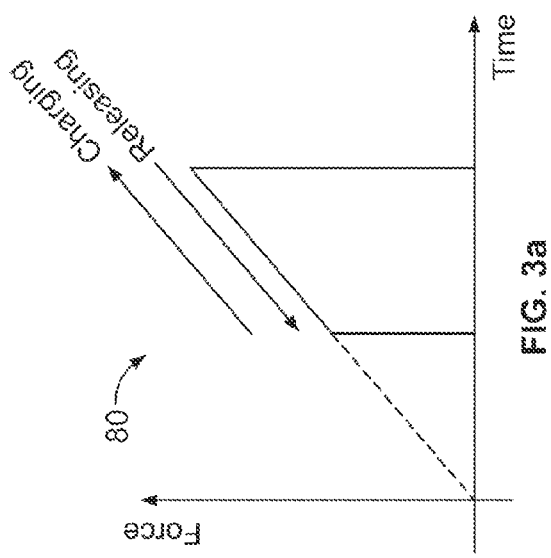
FIG. 3a illustrates an example profile of mechanical energy storage, in accordance with an embodiment of Applicants' proposed concept.
Figure 3B:
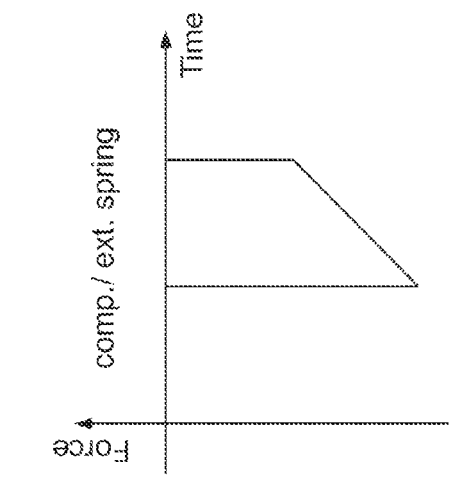
FIG. 3b illustrates an example profile of mechanical energy re-use, in accordance with an embodiment of Applicants' proposed concept.

This storage and release of mechanical energy can follow a profile such as the profile 80 shown in FIG. 3a. In an example, the amount of energy stored over time may be constant. In another example, the amount of energy stored over time may not be constant. The profile 80 shown in FIG. 3a may be provided by a biasing element such as a compression spring. When this spring energy is harnessed, the spring energy works against the dispense force profiles (i.e. to reduce them), and hence has been shown inverted as in FIG. 3b. In an example, this storage and release of mechanical energy profile could be flattened by using a pre-loaded low stiffness spring or a constant force spring.

Figure 4A:
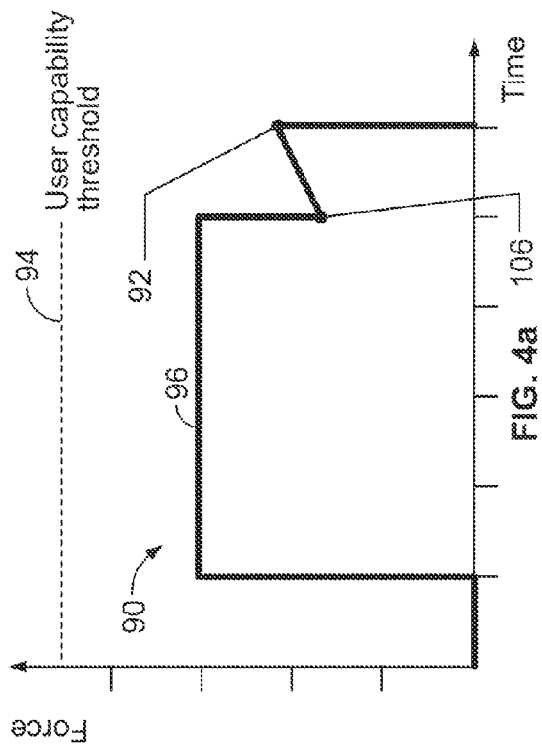
FIGS. 4a-4e illustrate example force profiles for delivery of a first and second medicament, in accordance with an embodiment of Applicants' proposed concept.
Figure 4B:
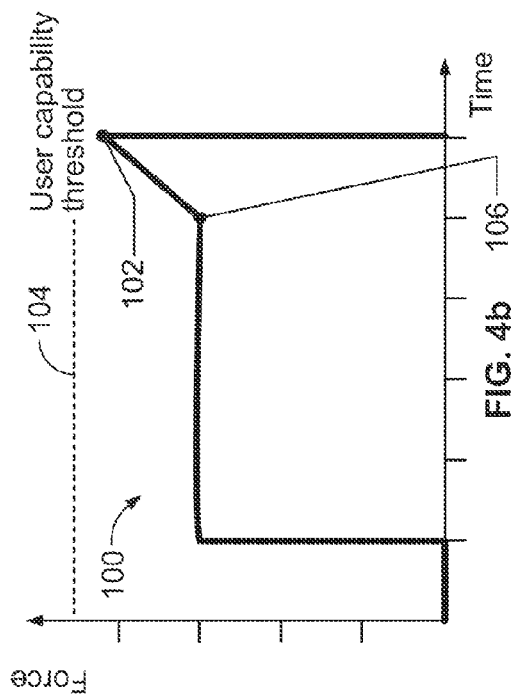
Figure 4C:
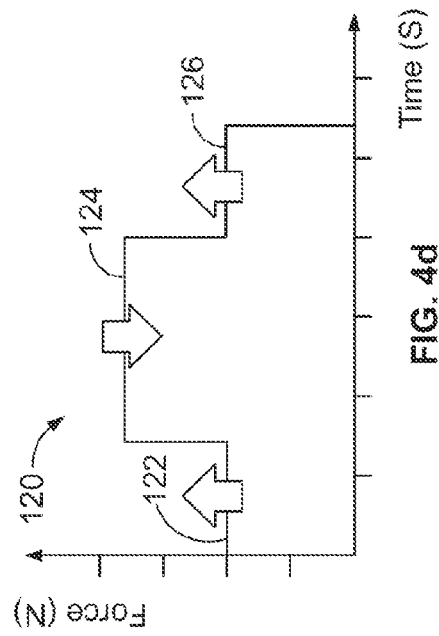

Three possible example resultant force profiles for delivery of two medicaments are shown in FIGS. 4a-4c. The variations in these example force profiles shown may be created by varying the magnitude of force added by the biasing element, such as a compression spring. In general, these graphs shown in FIGS. 4a-c have been created by adding the force profile shown in FIG. 3b to the combined force profile shown in FIGS. 2c and 2d. Similar to the example shown in FIGS. 2c and 2d, in these FIGS. 4a-c, the second medicament is either delivered during the latter part of delivery of the first medicament or after delivery of the first medicament FIG. 4a depicts a profile 90 in which the transition peak force 92, after the transition point 106, has been reduced below both the user capability threshold 94 and the plateau region 96. This profile 90 has the benefit that the dispense force for both medicaments is below the user capability threshold 94. Further, this profile 90 has the benefit that the force magnitude is similar between the two medicaments.

FIG. 4b depicts a profile 100 in which the peak force 102 has been reduced below the user capability threshold 104, and the transition point 106 to dispense of the second medicament has been timed to coincide such that there is a smooth transition from dispense of the first medicament to dispense of the second medicament. This example profile 100 has the benefit that the dispense force for both medicaments is below the user capability and that the smooth transition yields positive feedback to the user (e.g., the transition is not a sharp step change, and a sharp step change may improperly suggest to the user that the dispense process is finished or there is a device error).

FIG. 4c depicts a profile 110 in which the transition force peak 112 has been reduced to zero. A transition force peak of zero indicates that the dispensing of the second medicament is fully automatic (i.e., the device provides all the dispense force required for injection of the second medicament). An example advantage of a semi-automatic injection device that follows such a force profile is that there is little or no change in user input force, other than perhaps a small step to trigger the dosing of the second medicament. With a semi-automatic injection, the delivery of the second medicament can be designed to take place at any point during the delivery of the first medicament (e.g., sequential delivery, simultaneous delivery, interspersed delivery, etc). Specifically, a semi-automatic inject device can be designed such that the second medicament is only set once the first medicament passes 'x' units and then only dispenses at the same point during delivery of the first medicament. This, in addition to reducing the dispense force, advantageously allows the device to be primed on one compound only (up to the set point of the second medicament).

Figure 4D:
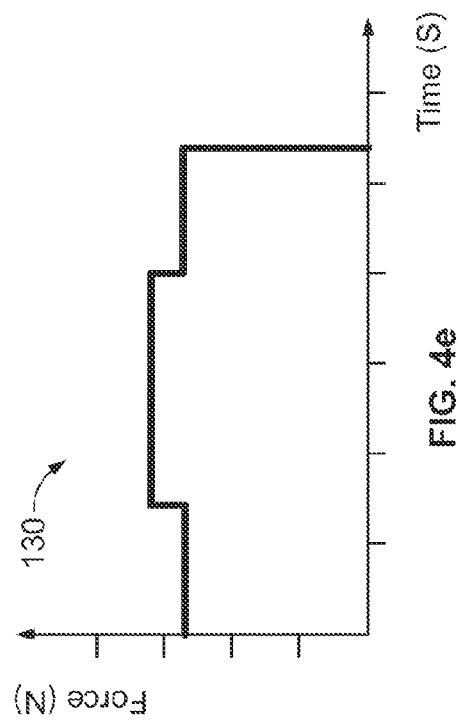
Figure 4E:
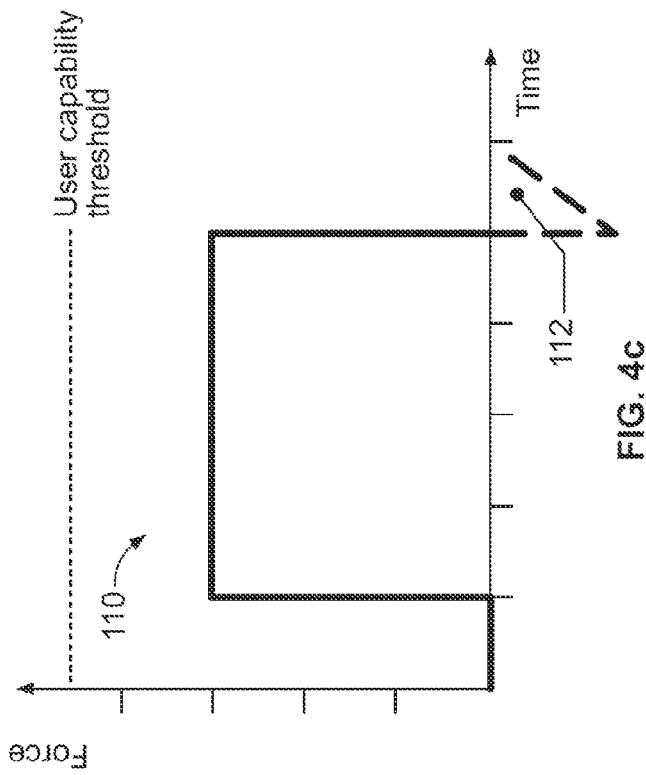

FIG. 4d shows a profile 120 in which the drug delivery sequence is of the form of a (i) first medicament phase 122, (ii) second medicament phase 124, and (iii) another first medicament phase 126, to suggest that there can be additional drug delivery steps either of the same medicament (repeated—as shown) or multiple medicaments. The profile 120 shows several regions that have a step transition with a significant step value. In this situation, the auto-assist functionality can be used to 'flatten' the peaks such that the step transition is a much smaller percentage of the full scale value. An example 'flattened' profile 130 is show in FIG. 4e. Such a flattened profile is advantageous, for example, in ensuring an optimum user profile where two medicaments with distinct profiles are dispensed alternatively within the same administration.

FIGS. 5-13 illustrate various embodiments of a drug delivery device according to Applicant's proposed concept that includes a spring element and is capable of assisting with delivery of the medicament. Generally, Applicants' proposed drug delivery device includes a variable dose setting mechanism operably coupled to a first reservoir holding a first medicament. The variable dose setting mechanism has a single dose setter. The drug delivery device also includes a fixed dose setting mechanism operably coupled to a second reservoir holding a second medicament. The device also includes a mechanical coupling, where the mechanical coupling operably couples the variable dose setting mechanism and the fixed dose setting mechanism. In addition, the mechanical coupling comprises a spring element. During dose setting via the single dose setter, (i) a variable dose of the first medicament is set, (ii) a fixed dose of the second medicament is automatically set, and (iii) the spring element is compressed or charged. Further, during dose dispense, the compressed spring element transfers stored energy to the fixed dose setting mechanism to at least assist with dispense of the fixed dose. In an example, to achieve dose profiles that involve an amount of auto-assistance (e.g., such as the dose profiles shown in FIGS. 4a-e) the mechanical energy may be released during the dispense stroke of the user. Further, in an example, the prior action of storing the mechanical energy may be carried out during the setting operation of the device.

A first embodiment of a drug delivery device in accordance with Applicants' proposed concept generally involves a mechanical coupling having a spring element, a lifting cylinder, a lifting collar, and an engagement pin. The lifting cylinder comprises (i) the spring element, (ii) a compression cylinder, (iii) an internal groove, (iv) a lifting surface, and (v) a lift pin. The engagement pin is engageable with the lifting collar. The lifting collar is configured to lift the lift cylinder during dose setting due to engagement with the engagement pin. Further, the lifting surface is configured to contact the lift pin and force the lift pin through the internal groove, thereby forcing the compression cylinder to be lifted in a proximal direction. Still further, the spring element is configured to be compressed due to the lifting of the compression cylinder in the proximal direction.

FIG. 5 illustrates example components of an example drug delivery device in accordance with this first embodiment. In particular, FIG. 5 illustrates a drug delivery device 200 that includes a variable dose setting mechanism 202 connected to a fixed dose setting mechanism 204. Although not shown in the FIG. 5, the variable dose setting mechanism 202 may include a reservoir of a first medicament (such as reservoir 6 holding first medicament 1) and the fixed dose setting mechanism 204 may include a reservoir of a second medicament (such as reservoir 5 holding second medicament 2). Drug delivery device includes a mechanical coupling 206 that operably couples the variable dose setting mechanism 202 and the fixed dose setting mechanism 204. The mechanical coupling may comprise elements of both the variable dose setting mechanism and the fixed dose setting mechanism. In this example and in the embodiments described later, a portion of the mechanical coupling is on the variable dose mechanism, and a portion is on the fixed dose mechanism.

Drug delivery device 200 also includes a single dose setter 208 operably coupled to variable dose setting mechanism 202. The mechanical coupling 206 includes a lift cylinder 210, a lifting collar 212, and an engagement pin 214. In this example, the variable dose setting mechanism 202 is a rotate to set and dispense mechanism that follows a helical path out of (and back into) the housing of the device. Such rotate to set and dispense mechanisms are well-known in the art. For the initial portion of the variable dose setting mechanism stroke for setting of a dose, the lifting collar 212 is in engagement with the lift cylinder 210 via the engagement pin 214 (see FIG. 6a-c). As will be described in more detail below, this stroke length where the lifting collar 212 is in engagement with the lift cylinder 210 is sufficient to the lift cylinder 210, which in turn sets the fixed dose setting mechanism 204 and stores energy within the spring 216 (see FIG. 5b) of the mechanical coupling 206.

Figure 5A:
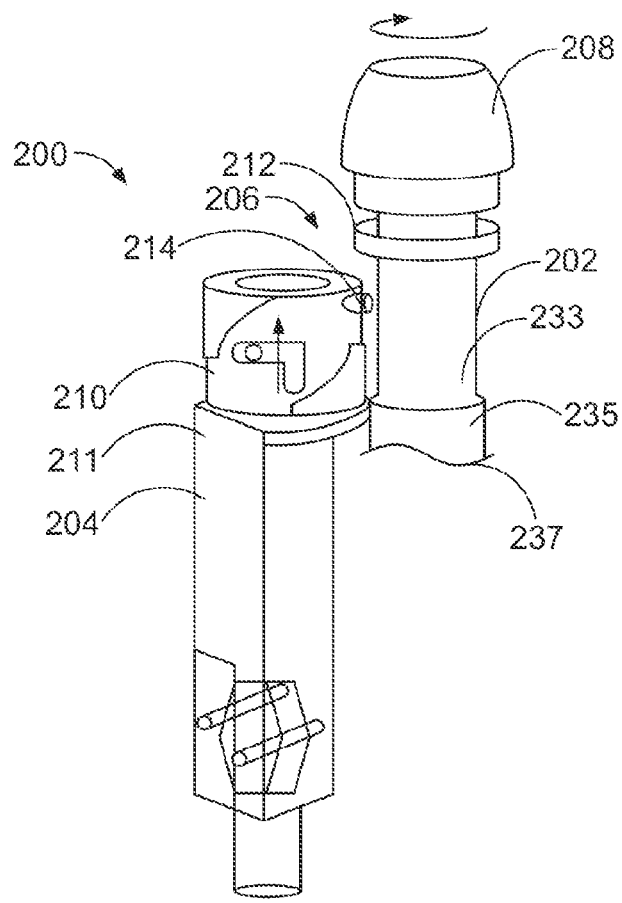
FIG. 5a illustrates a partial view of an example drug delivery device in accordance with an embodiment of Applicants' proposed concept.
Figure 5B:
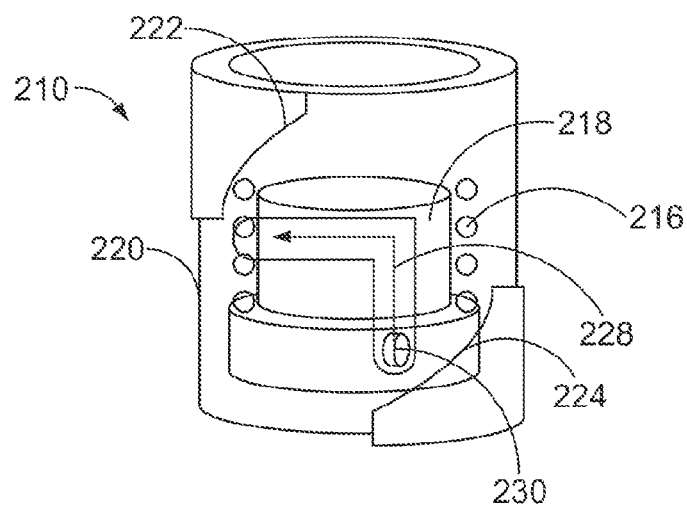
FIG. 5b illustrates an example lifting cylinder for the drug delivery device depicted in FIG. 5a and the internal mechanisms of the lifting cylinder.

As shown in FIG. 5b, the lift cylinder 210 includes a spring element, such as compression spring 216, and a compression cylinder 218. The body 220 of the lift cylinder 210 may include an upper lifting surface 222 and a lower lifting surface 224, as well as a groove 228 which a lifting pin 230 can travel through. In an example, the groove 228 is an "L-shaped" groove, as depicted in FIG. 5b. The pin 230 is fixed to the compression cylinder 218 and is independently acted upon by the two lifting surfaces 222, 224, depending on the phase of the dose/dispense stroke.

The operation of the drug delivery device 200 includes the following general phases: (i) initial engagement, (ii) lifting, (iii) energy storage/fixed dose setting, (iv) dispense (variable dose), and (v) energy release phase and dispense (combined dose). These steps or phases are described in greater detail below with reference to both FIGS. 5a-b and 6a-e.

FIG. 6a depicts an initial engagement phase of operation. Rotation 232 of the dose setter 208 causes the dose dial component 233 to rotate out of the body 237 or housing (the proximal end 235 of the body 237 is depicted in FIG. 5a) around a helical path. During this rotation, the lifting collar 212 raises the lift cylinder 210 through its connection with engagement pin 214. The lifting pin 230 is constrained to follow the L-shaped groove 228.

FIG. 6b depicts the lifting phase of the operation. During the lifting phase, the lower lifting surface 224 makes contact with the lifting pin 230 and raises it in proximal direction 241 through the vertical portion 234 of the L-shaped groove 228. This action causes the compression spring 216 to compress, and thus causes the compression spring 216 to store mechanical energy. The lifting pin 230 is constrained to move along the vertical portion 234, which forces the compression cylinder 218 to be lifted axially only without any rotation.

FIG. 6c depicts the energy stored/fixed dose set phase of the operation. As the cylinder pin 230 reaches the horizontal portion 236 of the L-shaped groove 228, the pin 230 is forced to rotate due to the slope 224 and remain on the horizontal portion 236. At this point, energy has been stored in the spring 216 and the compression cylinder 218 is constrained axially by the engagement of the lifting pin 230 in the horizontal portion 236 of groove 228. Further, the lifting collar 212 disengages from the engagement pin 214 and is allowed to continue on its helical path to set a larger dose of the variable dose medicament.

FIG. 6d depicts the dispense phase of the operation, where the device begins to dispense the variable dose of the first medicament. During this phase, the user may force the dose setter 208 to rotate in direction 240 (e.g., via a dose button). This forces the dial component 233 (see FIG. 5a) to wind back into the body 237 of the device, and this action forces the device 200 to begin dispensing the first medicament. During this initial phase of the dispense process, the lifting collar 212 is not connected to the lift cylinder 210; however, it re-connects with the lift cylinder 210 towards the end of the dispense stroke.

FIG. 6e depicts the energy release phase and dispense of the combined dose of medicament. During this phase, the lift cylinder 210 reconnects with the lifting collar 212. Upon re-connection, the upper surface 222 abuts the lifting pin 230 and forces the pin 230 along the horizontal portion 236 of the groove 228 toward the vertical portion 234. On reaching the vertical portion 234, the compression cylinder 218 is no longer axially constrained and therefore releases the stored energy in the spring 216 as the compression cylinder 218 is allowed to move downwards in direction 242. During this phase, the bottom of the compression cylinder bears on the reciprocating element 211 of the fixed dose setting mechanism 204. This transfers the stored energy to the fixed dose setting/dispensing mechanism 204 and assists with the dispense of the second medicament 2. The top inner face of the L-shaped groove 228 may also act on the pin 230 to assist with delivery in combination with the spring force. This may beneficially be a back-up to the pure spring force delivering the whole dose.

In general, as used herein, the reciprocating element represents a dose setting/dispense component, where on moving this outwards (a fixed amount) it sets the device, and then moving it back inwards (the same amount) it dispenses the dose. In an example, the reciprocating element could be a type of ratchet mechanism where the mechanism is prevented from moving backwards as the 'reciprocating element' is set (consequently it ratchets over the mechanism) and then on dispense the 'reciprocating element' pushes the mechanism forwards hence delivering the fixed dose. The reciprocating element then can be moved out again, without moving the main mechanism and 'spindle' backwards, the reciprocating element ratchets over the spindle and then on dispense again drives the 'spindle' forward to dispense the next fixed dose. The reciprocating element is referred to herein as a generic "reciprocating" element as it simply moves between two fixed states (i.e., a set state and a dispense state). Being a fixed dose, these states are the same, hence reciprocating between them.

A second embodiment of a drug delivery device in accordance with Applicants' proposed concept generally involves a mechanical coupling having a spring element, a cam having a groove, and an engagement feature that is engageable with the groove. A drive feature of the dose setter is configured to force the cam to rotate during dose setting. The engagement feature is configured to follow the groove and move in a proximal direction, and a reciprocating element is configured to be lifted due to the movement of the engagement feature in the proximal direction. Further, the spring element is configured to be compressed due to the lifting of the reciprocating element.

Figure 7:
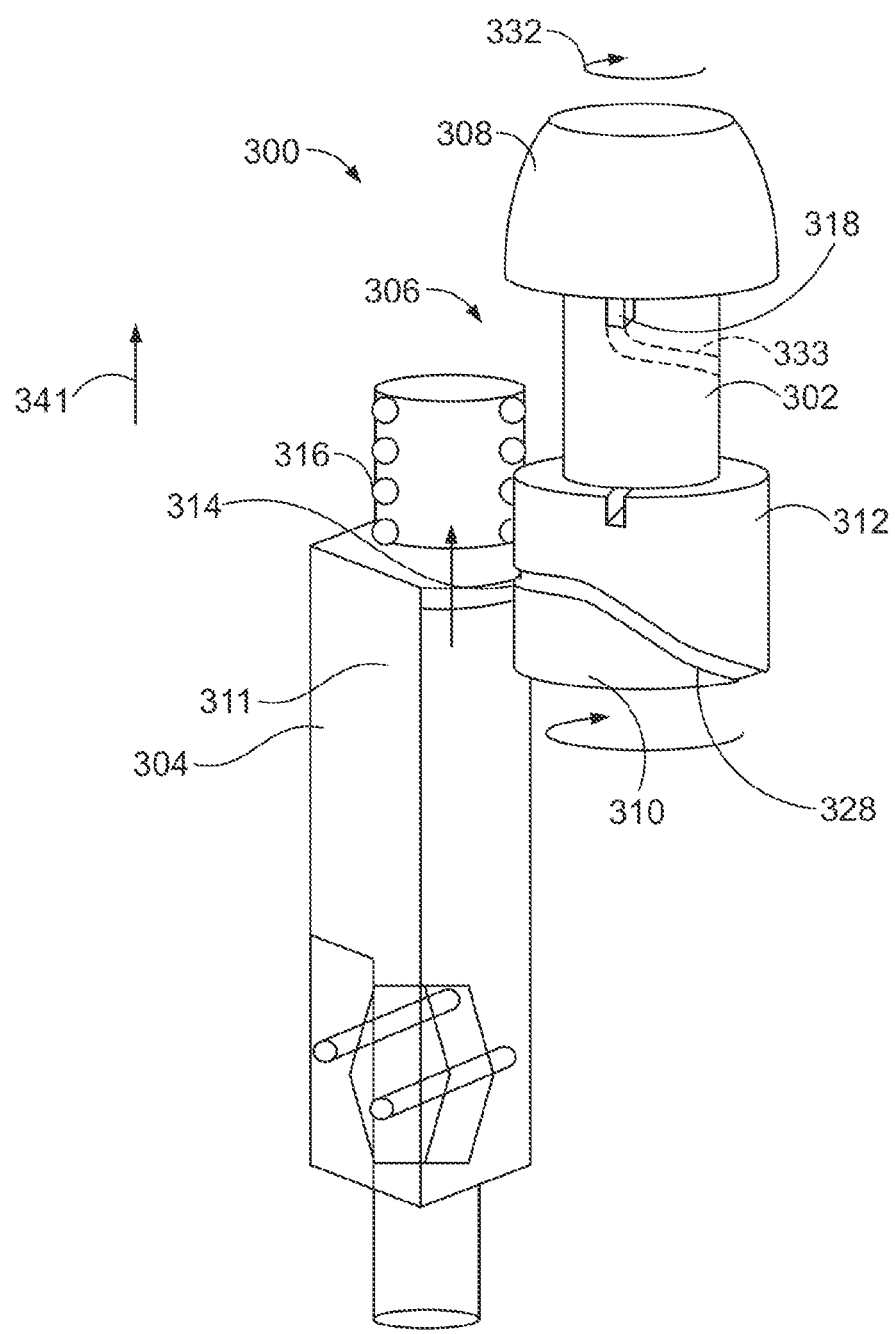
FIG. 7 illustrates a partial view of another example drug delivery device in accordance with an embodiment of Applicants' proposed concept.

FIG. 7 illustrates example components of an example drug delivery device in accordance with this second embodiment. In particular, FIG. 7 illustrates a drug delivery device 300 that includes a variable dose setting mechanism 302 connected to a fixed dose setting mechanism 304. Drug delivery device includes a mechanical coupling 306 that operably couples the variable dose setting mechanism 302 and the fixed dose setting mechanism 304. The mechanical coupling 306 comprises a spring element, such as compression spring 316.

In this second embodiment, the mechanical coupling 306 also includes a cam 310 with a groove 328, and the cam is employed to lift the reciprocating element 311 of the fixed dose setting mechanism 304 via an engagement feature 314. Drug delivery device 300 also includes a single dose setter 308 operably coupled to variable dose setting mechanism 302. The single dose setter 308 on the variable dose setting mechanism 302 forces the cam to rotate via drive features 318.

The operation follows a similar operation process as described above with reference to device 200 (i.e., initial engagement–lifting–energy storage/fixed dose set–dispense (variable dose)–energy release+dispense (combined dose)). In this example, the single dose setter 308 rotates clockwise in direction 332. The drive feature 318 forces the cam 310 to rotate clockwise as well. This forces the reciprocating element 311 of the fixed dose setting mechanism 304 to be lifted axially in proximal direction 341 as the engagement feature 314 is forced vertically through its engagement with the groove 328 in the cam 310. Vertical lift of the reciprocating element 311 causes the compression spring 316 to compress, and thus causes the compression spring 316 to store mechanical energy. At this point the variable dose mechanism 302 disengages from the cam 310 (which remains in its set position) and is capable of continuing on its helical path to set a larger dose of the first medicament 1.

During the dispense phase, the user may force (e.g., via a dose button) the dose setter 308 to rotate in a counterclockwise direction. This forces the dial component 333 to wind back into the body of the device, and this action forces the device 300 to begin dispensing the first medicament 1. Towards the end of the dispense stroke, the drive features 318 re-engage with the cam 310 and force it to rotate counterclockwise thus releasing the spring energy of spring 316. This release of spring energy may assist dispense of the second medicament 2 via the fixed dose setting mechanism 304.

A third embodiment of a drug delivery device in accordance with Applicants' proposed concept generally involves a mechanical coupling having a spring element, a lifting collar having an internal helical groove, and an engagement feature. The lifting collar is restrained in rotation relative to the fixed dose mechanism but is axially moveable. The dose setter is configured to follow a helical path during dose setting, and the engagement feature is configured to follow the helical path and contact an underside of the lifting collar to lift a reciprocating element of the fixed dose setting mechanism. Further, the spring element is configured to be compressed due to the lifting of the reciprocating element.

FIGS. 8a-b illustrate example components of an example drug delivery device in accordance with this third embodiment. In particular, FIGS. 8a-b illustrate a drug delivery device 400 that includes a variable dose setting mechanism 402 connected to a fixed dose setting mechanism 404. Drug delivery device 400 includes a mechanical coupling 406 that operably couples the variable dose setting mechanism 402 and the fixed dose setting mechanism 404. The mechanical coupling 406 comprises a spring element, such as compression spring 416, and a lifting collar 412 with an internal helical groove 428. Drug delivery device 400 also includes a single dose setter 408 operably coupled to variable dose setting mechanism 402.

The lifting collar 412 is rigidly fixed to the reciprocating element 411 of the fixed dose mechanism 404. The lifting collar 412 has a helical groove 428 located on an internal bore of the lifting collar 412. The variable dose setting mechanism 402 has both engagement features 414 and driving features 418 as shown in FIG. 8a. The engagement features 414 provide the initial axial lift of the lifting collar 412 until features 414 engage with the helical grooves at which point features 414 provide no further lift. The dose setter 408 also forces the lifting collar 412 downwards via the drive features 418.

The operation follows a similar operation process as described above with reference to devices 200 and 300 (i.e., initial engagement–lifting–energy storage/fixed dose set–dispense (variable dose)–energy release+dispense (combined dose)). In this example, the single dose setter 408 rotates clockwise in direction 432 around a helical path. The lifting collar 412 is restrained in rotation relative to the device body but is free to travel axially (within defined end points). The engagement features 414 follow the same helical path until they contact the underside of the lifting collar 412. At this point they continue to spin, but this forces the reciprocating element 411 to be lifted axially in direction 442. Vertical lift of the reciprocating element 411 causes the compression spring 416 to compress, and thus causes the compression spring 416 to store mechanical energy.

Once the fixed dose is set, the engagement features 414 enter the helical groove 428 in the lifting collar 412 at the helix entry point 441. The lifting collar 412 remains in this set position. Since the lifting collar 412 is prevented from rotating relative to the device body it is retained in the spring-compressed axial position by the engagement features 414 of the variable dose mechanism being engaged with the internal helix 428 of the lifting collar 412. In one example, the maximum dose of the variable dose mechanism is preferably set in order that the engagement features do not exit the opposite end of the internal helix, as this would release the lifting collar and the stored energy. Through this continued travel within the internal helix, the variable dose setting mechanism is capable of setting further increased doses after the fixed dose mechanism has been set.

An alternative method of restraining the lifting collar 412 is to allow the engagement features 414 to exit the opposite (top) end 444 of the lifting collar internal thread and to design a toggle element 446 of a reciprocating component such that it can initially resist the force of the spring 416. In this example, on dispense, the variable dose setting mechanism 402 rotates back into the device along the helical path dispensing the first medicament. The engagement features enter the helical grooves during the downward stroke and do not act on the lifting collar. Towards the end of the dispense stroke, the upper drive features force the reciprocating element downwards thus flipping the toggle and triggering the release of the spring energy which can be used to assist dispense of the second medicament via the fixed dose mechanism.

A fourth embodiment of a drug delivery device in accordance with Applicants' proposed concept generally involves a mechanical coupling having a spring element, an internal clutch mechanism, a lifting collar, a lifting groove, and an engagement feature capable of engagement with the lifting groove. The dose setter is configured to initially move axially during dose setting such that the variable dose setting mechanism lifts the reciprocating element. The spring element is configured to be compressed by the lifting of the reciprocating element. In addition, the internal clutch mechanism is configured to allow the dose setter to rotate to set the variable dose after the fixed dose is set.

Figure 9A:
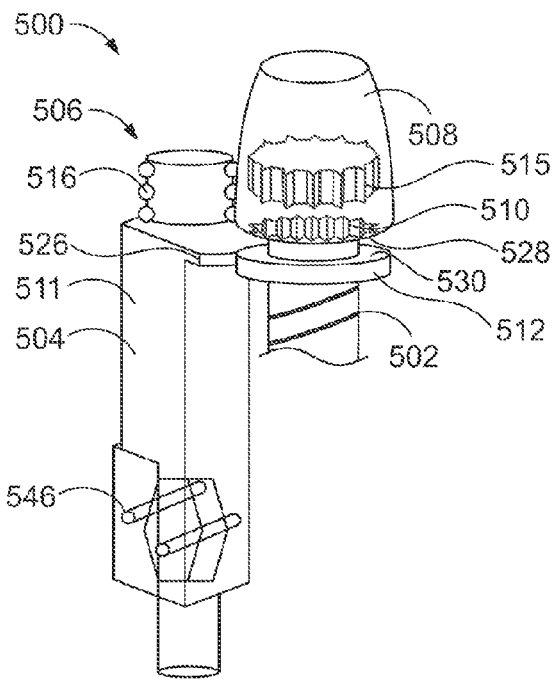
FIG. 9a illustrates a partial view of yet another example drug delivery device in accordance with an embodiment of Applicants' proposed concept.
Figure 9B:
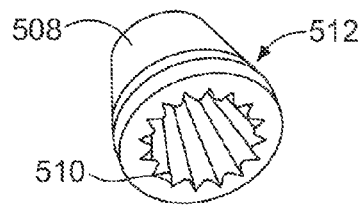
Figure 9C:
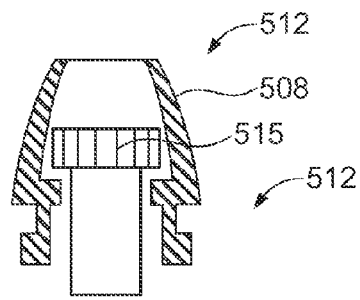
FIG. 9c illustrates a cross-section of the lifting collar of the drug delivery device depicted in FIG. 9a FIG. 10a illustrates a partial view of yet another example drug delivery device in accordance with an embodiment of Applicants' proposed concept.

FIG. 9a illustrates example components of an example drug delivery device in accordance with this fourth embodiment. In particular, FIG. 9a illustrates a drug delivery device 500 that includes a variable dose setting mechanism 502 connected to a fixed dose setting mechanism 504. Drug delivery device 500 includes a mechanical coupling 506 that operably couples the variable dose setting mechanism 502 and the fixed dose setting mechanism 504. The mechanical coupling 506 comprises a spring element, such as compression spring 516. The mechanical coupling 506 also includes a lifting collar 512 that contains splined clutch features 510 in addition to a lifting groove 528. FIG. 9c illustrates a cross-sectional view of the lifting collar 512. Drug delivery device 500 also includes a single dose setter 508 operably coupled to variable dose setting mechanism 502. FIG. 9b illustrates a perspective view of the dose setter 508. The dose setter 508 includes an internal clutch mechanism 515.

The splined clutch features 510 allow axial lift in proximal direction 541 (via the lifting collar 512) to be transmitted from the single dose setter 508 to the fixed dose setting mechanism 502 followed by the transmission of torque to the variable dose setting mechanism 504 via the internal splined features of internal clutch mechanism 515. Axial lift is used to set the fixed dose mechanism 504 and the transmission of torque is used to set the variable dose mechanism 502. The groove 528 on the lifting collar 512 connects with the reciprocating element 511 of the fixed dose setting mechanism 504 via the engagement feature 526. The mechanical coupling may include compression spring 516 for a means of storing mechanical energy.

The operation follows a similar operation process as described above with reference to devices 200, 300, and 400 (i.e., initial engagement–lifting–energy storage/fixed dose set–dispense (variable dose)–energy release+dispense (combined dose)). However, in this example, in contrast to the previous embodiments, the initial motion of the single dose setter 508 is axial. The force to initiate this axial motion is provided by the user pulling the dose setter 508 axially away from the body of the device 500 in proximal direction 541. This initial axial movement lifts the reciprocating element 511 of the fixed dose setting mechanism 504 vertically to its set point which causes the compression spring 516 to compress, and thus causes the compression spring 516 to store mechanical energy. The single dose setter 508 is constrained to axial motion during this phase (i.e., no rotation is allowed). Constraining the dose setter 508 to axial motion during this phase is to ensure that the fixed dose setting mechanism 504 reaches its set point. After the fixed dose setting mechanism 504 is set, the single dose setter 508 is allowed to rotate and set the variable dose setting mechanism 502.

Although not shown in the figure, the lifting groove 528 could consist of a helical portion in addition to the flat portion 530 to allow the variable dose setting mechanism 504 to continue setting doses without contacting the reciprocating element 511. The lifting groove 528 could also disengage provided a toggle element such as toggle mechanism 546 of the reciprocating element 511 was capable of resisting the spring force until acted by the downward stoke of the lifting collar 512. This part of the mechanism may be designed to ensure that any 'spike' in the dispense force profile was minimal. On dispense, the variable dose setting mechanism 502 rotates back into the device along a helical path dispensing the first medicament. Towards the end of the first medicament 1 dispense stroke, the lifting groove 528 re-engages with the engagement feature 526 and forces the reciprocating element 511 downwards thus releasing the spring energy, which can be used to assist dispense of the second medicament via the fixed dose setting mechanism 504.

A fifth embodiment of a drug delivery device in accordance with Applicants' proposed concept generally involves a mechanical coupling having a spring element, a lifting collar having at least one clip feature, an engagement feature, and at least one restraining feature. The engagement feature is configured to contact an underside of the lifting collar during dose setting and lift the lifting collar to a set point. Further, the spring element is configured to be compressed due to the lifting of the lifting collar to the set point. In addition, the at least one clip feature is configured to engage with the at least one restraining feature on the device body at the set point to keep the spring element in a compressed state.

Figure 10A:
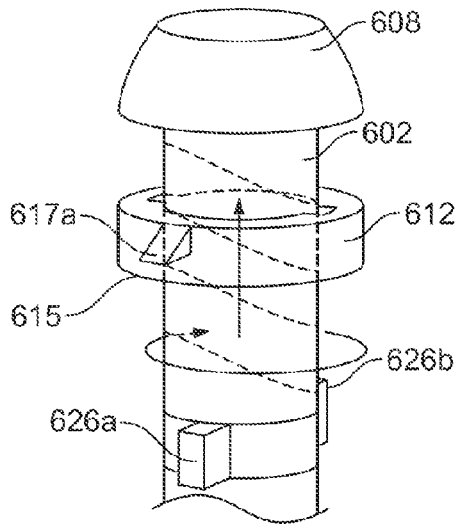
Figure 10B:
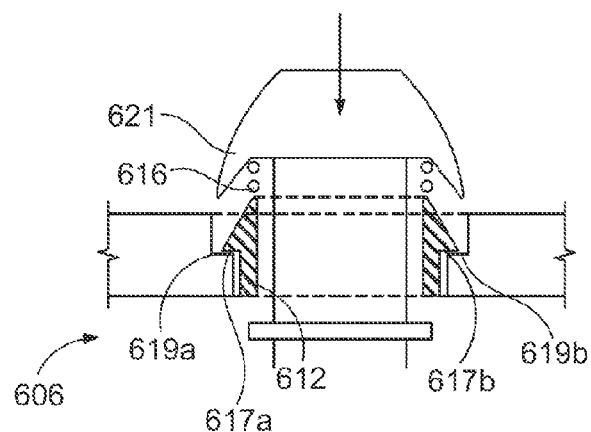

FIG. 10 illustrates example components of an example drug delivery device in accordance with this fifth embodiment. In particular, FIG. 10 illustrates a variable dose setting mechanism 602 that may be connected to a fixed dose setting mechanism. Similar to the examples discussed above, the variable dose setting mechanism 602 may be connected to the fixed dose setting mechanism via a mechanical coupling. FIGS. 10a-b show an embodiment in which engagement features have been added to the variable dose mechanism. In particular, FIG. 10a depicts an exploded view of a proximal end of the variable dose setting mechanism 602, and FIG. 10b depicts a cross sectional view of the proximal end. In this example, the engagement features 626a and 626b contact the underside 615 of the collar 612 and lift it to its set point at which point the clip features 617a and 617b engage with the restraining features 619a and 619b on the device body. The clip features 617a and 617b allow the collar 612 to remain in an 'up' position in which energy is stored in the compression spring 616.

Although not shown, the collar 612 also lifts the reciprocating element of the fixed dose setting mechanism to its set point. The variable dose setting mechanism 602 has drive features 621 on its lower surface as shown in FIG. 10b. The drive features 621 on the single dose setter 608 deform the clip features 617a and 617b allowing them to disconnect from the restraining features 619a and 619b. This disconnection allows the collar 612 to move downward and the stored energy in the spring to be used to assist dispense of the second medicament.

The operation follows a similar operation process as described above with reference to devices 200, 300, 400, and 500 (i.e., initial engagement–lifting–energy storage/fixed dose set–dispense (variable dose)–energy release+dispense (combined dose)). In this example, the single dose setter 608 rotates clockwise around a helical path. The engagement features 626a-b follow the same helical path during which they contact the underside 615 of the lifting collar 612. This forces the reciprocating element (not shown) to be lifted axially as the collar 612 moves upward, compressing the spring 616 and allows the clip features 617a-b to engage in the restraining features 619a-b in the body. The variable dose setting mechanism 602 is now capable of setting further doses as the engagement features 626a-b can pass through the helical groove (not shown) on the inside of the collar 612. On dispense, the variable dose setting mechanism 602 rotates back into the device along a helical path dispensing the first medicament. Towards the end of the first medicament dispense stroke, the drive features 621 deform the clip features 617a-b, which allows the collar 612 to move downwards thus releasing the spring energy. This spring energy may then be used assist with dispense of the second medicament via the coupled fixed dose mechanism.

A sixth embodiment of a drug delivery device in accordance with Applicants' proposed concept generally involves a mechanical coupling 706 having a spring element, a cam having a groove, and a cam follower. During dose setting, the cam is configured to force the cam follower to be lifted as the cam follower follows the groove, and the spring element is configured to be compressed due to the lifting of the cam follower.

FIGS. 11a-b illustrate example components of an example drug delivery device in accordance with this sixth embodiment. In particular, FIG. 11a depicts an exploded view of a proximal end of the variable dose setting mechanism 702, and FIG. 11b depicts a cross sectional view of the proximal end. In this example, drive features 721 on the variable dose setting mechanism 702 rotate a cam 709 with a helical groove 728. A cam follower 711 may follow the groove 728 in the cam 709 and compress a spring 716. A disengagement feature 715 on the single dose setter 708 may knock the cam follower 711 out of the helical groove 728 during the dispense stroke. This allows the cam follower 711 to move downward and the stored energy in the spring to be used to assist dispense of the second medicament. Although not shown, the cam follower 711 may also lift the reciprocating element of the fixed dose setting mechanism to its set point.

The operation follows a similar operation process as described above with reference to the example devices discussed above (i.e., initial engagement–lifting–energy storage/fixed dose set–dispense (variable dose)–energy release+ dispense (combined dose)). In this example, the single dose setter 708 rotates clockwise around a helical path. The drive features follow the same helical path during which they contact the engagement features in the cam 709 causing it to rotate. This rotation forces the cam follower to be lifted vertically (as it follows the groove) and compress the spring 716. This set position may have a detent into which the cam follower 711 may rest for improved stability. The variable dose setting mechanism 702 disengages from the cam 709 and is now capable of setting further doses.

On dispense, the variable dose setting mechanism 702 rotates back into the device along a helical path dispensing the first medicament 1. Towards the end of the first medicament dispense stroke, the disengagement feature 715 knocks the cam follower 721 out of the groove 728 thus releasing the spring energy which can be used to at least assist dispense of the second medicament 2 via the fixed dose setting mechanism (not shown). The drive features 721 then re-engage with the engagement features causing the cam 709 to rotate in the opposite direction to reset the device.

A seventh embodiment of a drug delivery device in accordance with Applicants' proposed concept generally involves a mechanical coupling having a spring element, a drive collar, and a cam. During dose setting, (i) the drive collar rotates the cam, (ii) the rotation of the cam lifts a reciprocating element of the fixed dose setting mechanism, and (iii) the lifting of the reciprocating element compresses the spring element.

Figure 12B:
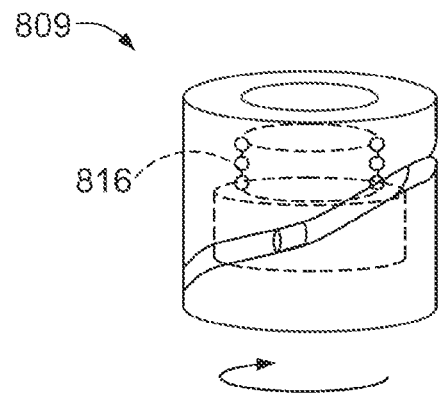

FIGS. 12a-b illustrates an example drug delivery device in accordance with this seventh embodiment. In particular, FIG.

12a illustrates a drug delivery device 800 that includes a variable dose setting mechanism 802 connected to a fixed dose setting mechanism 804. Drug delivery device 800 includes a mechanical coupling 806 that operably couples the variable dose setting mechanism 802 and the fixed dose setting mechanism 804. The mechanical coupling 806 comprises a spring element, such as compression spring 816, a drive collar 812, and a cam 809. Drug delivery device 800 also includes a single dose setter 808 operably coupled to variable dose setting mechanism 802.

In this example, drive features 821 on the variable dose setting mechanism 802 rotate a drive collar 812 that in turn rotates a cam 809 via gear teeth 811. The reciprocating element on the fixed dose setting mechanism 804 contains a pin 817 that follows the helical groove 823 in the cam 809. The reciprocating element 811 is lifted vertically as the pin 817 is forced to follow the helical groove 823. This vertical movement compresses the spring 816 thus storing mechanical energy.

The operation follows a similar operation process as described above with reference to example devices described above (i.e., initial engagement–lifting–energy storage/fixed dose set–dispense (variable dose)–energy release+dispense (combined dose)). In this example, the single dose setter 808 rotates clockwise around a helical path. The drive feature 821 forces the drive collar 812 to rotate. Rotation of the drive collar 812 forces the cam 809 to rotate via the gear features 811. This rotation forces the reciprocating element to be lifted vertically and compress the spring 816 (as the pin 817 follows the helical groove 823 in the cam 809). A detent feature 825 on the top portion of the helical groove 823 is provided so that the reciprocating element 811 is held in a stable position. At this point the fixed dose setting mechanism 804 is set. The variable dose engine then disengages from the cam 809 and is now capable of setting further doses.

On dispense, the variable dose setting mechanism 802 rotates back into the device along a helical path dispensing the first medicament 1. Towards the end of the first medicament dispense stroke, the drive features 821 re-engage with the engagement features on the drive gear and force the drive collar 812 to rotate in the opposite direction. This rotation forces the cam 809 to counter rotate which forces the pin 817 out of the detent 825 allowing the stored spring energy to be released. The spring energy can then be used to assist dispense of the second medicament 2 via the fixed dose mechanism 804.

An eighth embodiment of a drug delivery device in accordance with Applicants' proposed concept generally involves a mechanical coupling having a spring element, a drive collar, and a winding collar comprising (i) the spring element, wherein the spring element is a torsion spring, and (ii) a spring retainer having a groove, wherein the groove comprises an escapement. During dose setting, (i) rotation of the drive collar forces the winding collar to rotate, and (ii) the rotation of the winding collar forces a spring arm to follow a groove until the spring arm is forced into an escapement, such that torsional spring energy is stored.

Figure 13A:
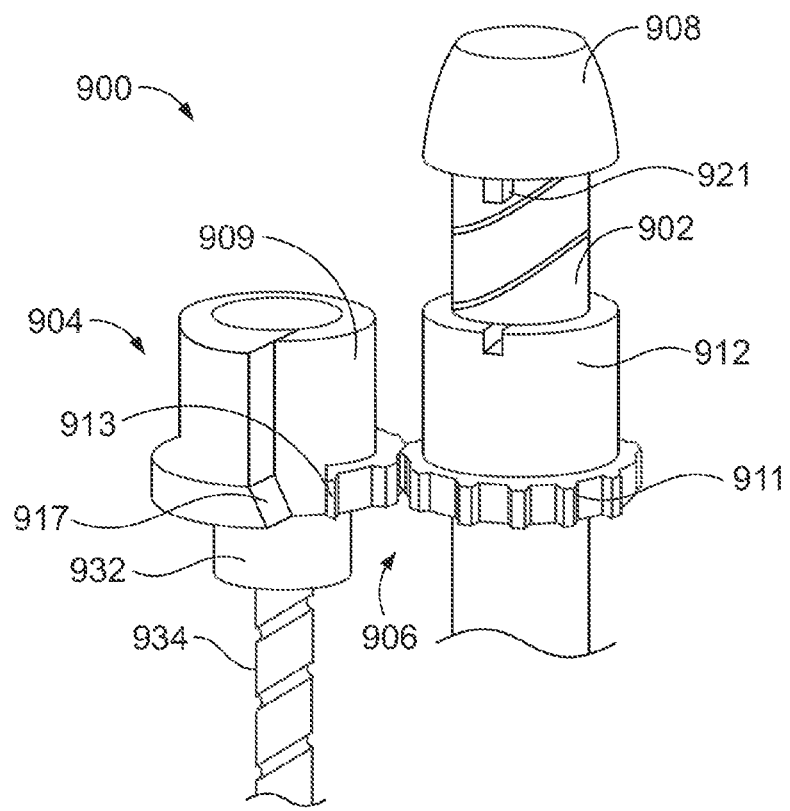
FIG. 13a illustrates a partial view of yet another example drug delivery device in accordance with an embodiment of Applicants' proposed concept.

FIG. 13 illustrates example components of an example drug delivery device in accordance with this eighth embodiment. In particular, FIG. 13 illustrates a drug delivery device 900 that includes a variable dose setting mechanism 902 connected to a fixed dose setting mechanism 904. Drug delivery device 900 includes a mechanical coupling 906 that operably couples the variable dose setting mechanism 902 and the fixed dose setting mechanism 904. Drug delivery device 900 also includes a single dose setter 908 operably coupled to variable dose setting mechanism 902.

Figures 13B, 13C:
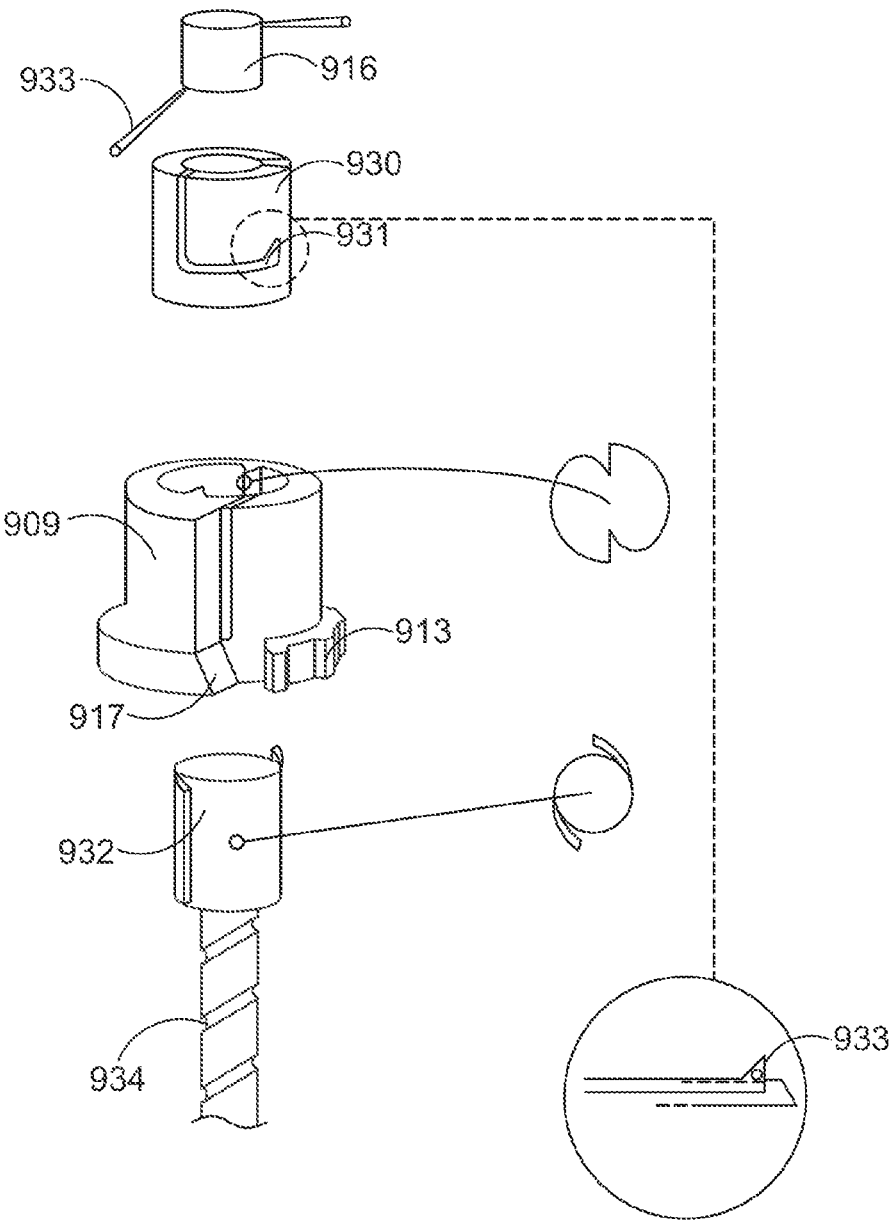

In this example, a torsion spring is used to drive a spindle-based fixed dose setting mechanism 904. Drive features 921 on the variable dose setting mechanism 902 rotate a drive collar 912 that in turn rotates a spring winding mechanism 909 via gear teeth 911 and 913. The spring winding mechanism 909 includes a torsion spring 916, spring retainer 930, winding collar 909, ratchet 932 and lead screw or spindle 934, as shown in FIG. 13b. The spring retainer 930 has a groove 931 in which the spring arm 933 travels during wind up. The winding collar 909 has a driving face 917 that forces the arm 933 of the torsion spring 916 along the groove 931. In addition to this, it has gear teeth 913 that engage with the gear teeth 911 on the drive collar 912. The winding collar 909 connects to the spindle 934 by means of the ratchet 932. The ratchet engagement allows the spindle 934 to remain stationary during wind up and advance forward during energy release. Energy from the torsion spring 916 forces the winding collar 909 to rotate clockwise which in turn rotates the ratchet 932 that then advances the spindle 934.

In order to set a dose, the single dose setter 908 rotates clockwise around a helical path. The drive features 921 force the drive collar 912 to rotate. Rotation of the drive collar 912 forces the winding collar 909 to rotate via the gear features. This rotation forces the spring arm 933 to follow the groove 931 until it is forced into the escapement and held there as shown in FIG. 13c. At this point the fixed dose setting mechanism 904 is set. The variable dose mechanism 902 disengages from the drive collar 912 and is now capable of setting further doses.

On dispense, the variable dose setting mechanism 902 rotates back into the device along a helical path dispensing the first medicament. Towards the end of the first medicament dispense stroke, the drive features 921 re-engage with the engagement features on the drive collar 912 and force the drive collar 912 to rotate in the opposite direction. This rotation forces the winding collar 909 to counter rotate which forces the spring arm 933 out of the escapement allowing the spring energy to be released. The torsional energy forces the winding collar 909 to counter rotate thus forcing the ratchet 932 to rotate and advance the spindle 934. The spindle 934 advances due to the fact that it is restrained from rotating via the longitudinal groove. The spring energy can then be used to assist dispense of the second medicament via the fixed dose mechanism 904.

Although the embodiments described above are described primarily as assisted dispense embodiments, these embodiments could be used as the basis of semi-auto injector designs. Other potential embodiments for this invention include, but are not limited to the addition and re-use of energy stored by pneumatic, hydraulic or electro-mechanical means. Additional functionality (and benefit) could be realized through the addition of a valve that prevents the device from 'weeping' under the action of auto-assist when the device is not being actuated by the user. Weeping is defined as the slow release of fluid from the needle.

Exemplary embodiments of the present invention have been described. Those skilled in the art will understand, however, that changes and modifications may be made to these embodiments without departing from the true scope and spirit of the present invention, which is defined by the claims.

The invention claimed is:
1. A drug delivery device comprising:
    a variable dose setting mechanism operably coupled to a first reservoir holding a first medicament, the variable dose setting mechanism having a dose setter;
    a fixed dose setting mechanism operably coupled to a second reservoir holding a second medicament;

a mechanical coupling, wherein the mechanical coupling operably couples the variable dose setting mechanism and the fixed dose setting mechanism and wherein the mechanical coupling comprises a spring element;

wherein the variable dose setting mechanism is configured to set a variable dose of the first medicament upon activation of the dose setter, wherein the fixed dose setting mechanism is configured to set a fixed dose of the second medicament during the activation of the dose setter, and wherein the spring element is configured to store energy during dose setting and to transfer stored energy to the fixed dose setting mechanism to at least assist with dispense of the fixed dose.

2. The drug delivery device of claim 1, wherein the variable dose setting mechanism is a rotationally-set variable dose setting mechanism, and wherein the fixed dose setting mechanism is an axially-set fixed dose setting mechanism.

3. The drug delivery device of claim 1, wherein the fixed dose setting mechanism further comprises a reciprocating element, wherein the mechanical coupling further comprises:
an internal clutch mechanism; a lifting collar;
a lifting groove;
an engagement feature capable of engagement with the lifting groove,
wherein the dose setter is configured to initially move axially during the activation of the dose setter such that the variable dose setting mechanism lifts the reciprocating element, wherein the spring element is configured to be compressed by the lifting of the reciprocating element,
wherein the internal clutch mechanism is configured to allow the dose setter to rotate to set the variable dose after the fixed dose is set.

4. The drug delivery device of claim 1, wherein the dose setter comprises a drive feature, wherein the fixed dose setting mechanism further comprises a reciprocating element, and wherein the mechanical coupling further comprises:
a cam having a groove;
an engagement feature that is engageable with the groove,
wherein (i) the drive feature of the dose setter is configured to force the cam to rotate during dose setting, (ii) the engagement feature is configured to follow the groove and move in a proximal direction, (iii) the reciprocating element is configured to be lifted due to the movement of the engagement feature in the proximal direction, and (iv) the spring element is configured to be compressed due to the lifting of the reciprocating element.

5. The drug delivery device of claim 1, wherein the mechanical coupling further comprises:
a lifting collar having at least one clip feature; an engagement feature;
at least one restraining feature disposed on a device body;
wherein (i) the engagement feature is configured to contact an underside of the lifting collar during dose setting and lift the lifting collar to a set point, (ii) the spring element is configured to be compressed due to the lifting of the lifting collar to the set point, (iii) the at least one clip feature is configured to engage with the at least one restraining feature on the device body at the set point to keep the spring element in a compressed state.

6. The drug delivery device of claim 1, wherein the mechanical coupling further comprises:
a cam having a groove; a cam follower,
wherein, during dose setting, (i) the cam is configured to force the cam follower to be lifted as the cam follower follows the groove, and (ii) the spring element is configured to be compressed due to the lifting of the cam follower.

7. The drug delivery device of claim 1, wherein the mechanical coupling further comprises:
a lift cylinder, wherein the lift cylinder comprises (i) the spring element, (ii) a compression cylinder, (iii) an internal groove, and (iv) a lifting surface, and (v) a lift pin;
a lifting collar;
an engagement pin, wherein the engagement pin is engageable with the lifting collar;
wherein (i) the lifting collar is configured to lift the lift cylinder during dose setting due to engagement with the engagement pin, (ii) the lifting surface is configured to contact the lift pin and force the lift pin through the internal groove, thereby forcing the compression cylinder to be lifted in a proximal direction, and (iii) the spring element is configured to be compressed due to the lifting of the compression cylinder in the proximal direction.

8. The drug delivery device of claim 7, wherein the groove is an L-shaped groove.

9. The drug delivery device of claim 1, wherein the fixed dose setting mechanism further comprises a reciprocating element, wherein the mechanical coupling further comprises:
a lifting collar having an internal helical groove, wherein the lifting collar is restrained in rotation relative to the fixed dose mechanism but is axially moveable; and
an engagement feature;
wherein (i) the dose setter is configured to follow a helical path during dose setting, (ii) the engagement feature is configured to follow the helical path and contact an underside of the lifting collar to lift the reciprocating element of the fixed dose setting mechanism, and (iv) wherein the spring element is configured to be compressed due to the lifting of the reciprocating element.

10. The drug delivery device of claim 9, wherein the engagement feature is configured to enter the internal helical groove at a helix entry point after the fixed dose is set.

11. The drug delivery device of claim 1, wherein the fixed dose setting mechanism further comprises a reciprocating element, wherein the mechanical coupling further comprises:
a drive collar; a cam,
wherein (i) the drive collar is configured to rotate the cam during dose setting, (ii) the cam is configured to lift the reciprocating element of the fixed dose setting mechanism, and (iii) the spring element is configured to be compressed due to the lifting of the reciprocating element.

12. The drug delivery device of claim 11, wherein a pin of the fixed dose setting mechanism is configured to follow a groove of the cam during dose setting to lift the reciprocating element of the fixed dose mechanism.

13. The drug delivery device of claim 1, wherein the mechanical coupling further comprises:
a drive collar; and
a winding collar comprising (i) the spring element, wherein the spring element is a torsion spring, wherein the torsion spring comprises a spring arm and (ii) a spring retainer having a groove, wherein the groove comprises an escapement,
wherein (i) the drive collar is configured to force the winding collar to rotate during dose setting, and (ii) the winding collar is configured to force the spring arm to follow the groove until the spring arm is forced into the escapement such that torsional spring energy is stored.

14. The drug delivery device of claim 13, wherein during dispense, (i) rotation of the winding collar forces the spring arm out of the escapement, and (ii) the torsional spring energy of the torsion spring forces the winding collar to rotate, thereby forcing a ratchet of the fixed dose setting mechanism to rotate and assist advancement of a spindle of the fixed dose setting mechanism.

* * * * *